US006967256B2

(12) United States Patent
Cummins et al.

(10) Patent No.: US 6,967,256 B2
(45) Date of Patent: Nov. 22, 2005

(54) FORMATION OF ENEDIYNES BY REDUCTIVE COUPLING FOLLOWED BY ALKYNE METATHESIS

(75) Inventors: Christopher C. Cummins, Cambridge, MA (US); James M. Blackwell, Portland, OR (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/666,565

(22) Filed: Sep. 19, 2003

(65) Prior Publication Data

US 2004/0215028 A1 Oct. 28, 2004

Related U.S. Application Data

(60) Provisional application No. 60/411,847, filed on Sep. 19, 2002.

(51) Int. Cl.[7] .......................... C07F 11/00; C07F 13/00; C07F 15/00; B01J 31/00; C07C 6/00
(52) U.S. Cl. ...................... 556/58; 556/43; 556/46; 556/136; 556/140; 549/206; 585/534; 585/643; 502/152
(58) Field of Search .............................. 556/43, 46, 58, 556/140, 136; 585/534, 643; 549/206; 502/152

(56) References Cited

U.S. PATENT DOCUMENTS

| 5,436,361 A | 7/1995 | Jones et al. ................. 556/466 |
| 6,175,047 B1 | 1/2001 | Hori et al. ................... 585/645 |
| 6,391,916 B1 | 5/2002 | Dai et al. ................... 514/529 |
| 2002/0034829 A1 | 3/2002 | Hall et al. ................... 436/518 |
| 2002/0058812 A1 | 5/2002 | Grubbs et al. ................. 546/2 |
| 2002/0072632 A1 | 6/2002 | Guram et al. ................. 564/15 |

FOREIGN PATENT DOCUMENTS

| DE | WO 99/40047 | 8/1999 | ........... C07B/37/10 |
| EP | 1 022 282 A2 | 1/1999 | ........... C07F/15/00 |

OTHER PUBLICATIONS

Yi–Chou Tsai, et al., "Facile Synthesis of Trialkoxymolybdenum (VI) Alkylidyne Complexes for Alkyne Metathesis," *Organometallics* 2000, vol. 19, pp. 5260–5262, (Jul. 27, 2000).

Philippus F. Engel, et al., "Carbon–Carbon and Carbon–Heteroatom Coupling Reactions of Metallacarbynes," *Chemical Rev.* 1995, 95, pp. 2281–2309, (Jan. 27, 1994).

Karin Weiss, et al., "Acyclic Diyne Metathesis (ADIMET), an Efficient Route to Poly(phenylene)ethynylenes (PPEs) and Nonconjugated Polyalkynylenes of High Molecular Weight," *Angew. Chem. Int. Ed. Engl.*, 36, No. 5, pp. 506–509, (1997).

(Continued)

*Primary Examiner*—Porfirio Nazario-Gonzalez
(74) *Attorney, Agent, or Firm*—Dana M. Gordon; Foley Hoag LLP

(57) ABSTRACT

One aspect of the present invention relates to methods of preparing enedialkylidyne complexes, enediynes, and alkyne metathesis catalysts, as well as methods of catalyzing alkyne metathesis reactions. The present invention also relates to methods of activating enedialkylidyne complexes for metathesis. The present invention also relates to enedialkylidyne complexes.

55 Claims, 2 Drawing Sheets

OTHER PUBLICATIONS

Andreas Mayr et al., "Electronic Communications between Metal Centers Across Unsaturated Alkylikyne Ligands," *J. Am. Chem. Soc., 1999, 121*, pp. 1760–1761, (Feb., 1999).

Richard R. Schrock, "High Oxidation State Multiple Metal–Carbon Bonds," *Chem. Rev. 2002, 102*, pp. 145–179, (2002).

Marie Pui Yin Yu, et al., "4–Iodobenzylidyne as a Precursor Ligand for Extended Unsaturated Alkylidyne Ligands", *J. Chem. Soc. Dalton Trans.*, pp. 2373–2378 (1988).

Graerne Hogarth, et al., "Linking Metal Centres with Diimido Ligands: Synthesis, Electronic and Molecular Structure and Electrochemistry of Organometallic Ditungsten Complexes, *J. Chem Soc., Dalton Trans.,*" pp. 2705–2723 (1999).

Andreas Mayr, et al., "Recent Advances in the Chemistry of Metal–Carbon Triple Bonds," *Advances in Organometallic Chemistry, vol. 32*, pp. 227–324, (1991).

Frederic Paul, et al., "Organometallic Molecular Wires and Other Nanoscale–Sized Devices. An Approach Using the Organoiron (dppe)Cp*Fe Building Block", pp. 431–509, , *Elsevier Scienc S.A.*, 178–180, (1998).

James M. Blackwell, et al., "Enediynes via Sequential Acetylide Reductive Coupling and Alkyne Metathesis: Easy Access to Well–Defined Molybdenum Initiators for Alkyne Metathesis," *Organometallics 2003, 22*, pp. 3351–3353 (2003).

David S. Frohnapfel, et al., "Variable Electronic Coupling Through Hydrocarbon Spacers Bridging–Carbon Triple" *J. Phys. Chem A 1998. 102*. pp. 5665–5669, (1998).

Keng–Yu Shih, et al., "Synthesis of Molybdenum Complexes that Contain Silylated Triamidoamine Ligsands. A μ–Dinitrogen Complex, Methyl and Acetylide Complexes, and Coupling of Acetylides," *J. Am. Chem. Soc. 1994, 116*, pp. 8804–8805, (1994).

Steven A. Krouse, et al. "The Synthesis of $trans-(Me_3CO)_3W\equiv CCH\equiv CHC\equiv W$ $(OCMe_3)_3$, cis, $cis-(Me_3CO)_3W\equiv CCH\equiv CHC\equiv CCh\equiv CHC\equiv W$ $(OCMe_3)_3$," *Journal of Organometallic Chemistry, 355*, pp. 257–265, (1988).

B. E. Woodworth, et al., "Stepwise Synthesis of ($\equiv CCH_2CH_2C\equiv$), ($\equiv CCH\equiv CHC\equiv$), and ($\equiv CC\equiv CC\equiv$) Bridges between Molybdenum or Tungsten Centers," *J. Am. Chem. Soc. 1997, 119*, pp. 828–829, (1996).

Hai Ping Xia, et al., "Synthesis of Symmetrical $C_5H_5$–Bridged Dimeric Ruthenium Complexes," *Organometallics 1997, 16*, pp. 3557–3560, (1997).

Blackwell, J. M. et al., "Enediynes via Sequential Acetylide Reductive Coupling and Alkyne Metathesis: Easy Access to Well–Defined Molybdenum Initiators for Alkyne Metathesis," *Amer. Chem. Soc. Organometallics*, 22, 3351–3353 (2003).

Krouse, S. A. et al., "The synthesis of $trans-(Me_3CO)_3W\equiv CCH\equiv CHC\equiv W(OCMe_3)_3$,*cis*, $cis-(Me_3CO)_3W\equiv CCH\equiv CHC\equiv CCH\equiv CHC\equiv W(OCMe_3)_3$, and related metal–capped ene–ynes, and evaluation of them as catalysts for preparing polydiacetylenes," *Journal of Organometallic Chem, 355*, 257–265 (1988).

International Search Report completed on Sep. 10, 2004 and mailed on Sep. 20, 2004.

FORMATION OF ENEDIYNES BY REDUCTIVE COUPLING FOLLOWED BY ALKYNE METATHESIS

RELATED APPLICATIONS

This application claims the benefit of priority to U.S. Provisional Patent Application Ser. No. 60/411,847, filed Sep. 19, 2002; the specification of which is hereby incorporated by reference.

GOVERNMENT SUPPORT

The invention was made with support provided by the National Science Foundation (Grant No. CHE-9988806); therefore, the government has certain rights in the invention.

BACKGROUND OF THE INVENTION

Recently, much attention has focused on systems containing enediyne units as a result of their potential pharmaceutical applications. As used herein, an enediyne refers to a chemical compound containing a carbon-carbon double bond (ene) and a pair of carbon-carbon triple bonds (diyne). Specifically, enediynes have been incorporated into a number of bioactive agents. The bioactive agents have been studied primarily as antitumor agents in cancer chemotherapy trials.

One example of a possible anti-tumor drug containing an enediyne group is Calicheamicinone. As stated in an article by Haseltine et al. entitled "Total Synthesis of Calicheamicinone: New Arrangements for Actuation of the Reductive Cycloaromatization of Aglycon Congeners" published in The Journal of the American Chemical Society, Volume 113, pages 3850–3866, 1991, which is incorporated herein by reference in its entirety, Calicheamicinone has exhibited remarkably potent cytotoxicity and high cell-killing potential for cancer chemotherapy. In particular, Calicheamicinone and other similar chemical compounds containing enediynes possess DNA-damaging ability. Specifically, these compounds can cause strand scission of DNA via diyl radical attack.

The enediyne contained in Calicheamicinone represents the pharmacophore or active group responsible for its bioactive characteristics. Consequently, one of the components or constituents used in the synthesis of Calicheamicinone is a chemical compound containing the enediyne group and in particular, (Z)-1,6-dilithio-hex-3-ene-1,5-diyne. Unfortunately, this particular dilithio enediyne has been difficult and expensive to produce. In the past, synthesis of dilithio enediynes has been accomplished by first using a procedure derived by Vollhardt et al. as detailed in an article entitled "Stereospecific Synthesis of Cis- and Trans-1,6-Bistrimethylsilyl-Hex-3-Ene-1,5-Diyne" published in Tetrahedron Letters, volume 26, pages 709–712, 1985. Vollhardt et al. more particularly details the synthesis of isomers of 1,6-[bis(trimethylsilyl)]-hex-3-ene-1,5-diyne which is a precursor to the dilithio enediynes in a more protected form. The synthesis of enediynes in Vollhardt et al. includes a palladium-catalyzed reaction of substituted alkynes and vinyl halides. Specifically, the 1,6-[bis(trimethylsily)]-hex-3-ene-1,5-diynes are made through a catalytic double coupling of trimethylsilylethyne with isomers of dichloroethene. However, this method renders practical scale synthesis prohibitively expensive. Also, environmentally damaging compounds, such as organo chlorine compounds, must be used during synthesis of the enediynes. Consequently, a need exists for an efficient and inexpensive route to producing the needed enediynes.

Besides being used in anti-tumor agents, enediynes have also been found useful in a wide variety of other applications. For instance, enediynes also represent an important class of conjugated $\pi$ systems with potentially useful optical and electronic properties. Such uses are described by Diederich et al. in "$\pi$-Complexes Incorporating Tetraphenyltetraethynylethene" published in The Journal of the Chemical Society, Chemical Communication, pages 205–208, 1994, and incorporated herein by reference in its entirety. Therefore, applications to materials chemistry and polymer science are envisioned because the use of diynes bearing a rigid conjugated spacer is expected to lead to conjugated polymers with applications as conducting organic materials. However, an efficient reaction scheme for synthesizing enediynes needed in such applications has remained absent from the prior art.

Various enediynes have also been found useful in the synthesis of polymers and in the synthesis of substituted benzenes. Further uses are disclosed in "Synthesis of Diacetylene Macrocycles Derived from 1,2-Diethynylbenzene Derivatives: Structure and Reactivity of the Strained Cyclic Dimer" by Zhou et al. published in the Journal of Organic Chemistry, pp 1294–1301, 1994, which also is incorporated herein by reference.

SUMMARY OF THE INVENTION

One aspect of the present invention relates to methods of preparing enedialkylidyne complexes, enediynes, or alkyne metathesis catalysts.

In one embodiment, the present invention relates to a method of preparing an enedialkylidyne complex comprising combining a terminal alkyne with a first transition metal complex to give a second transition metal complex; and treating the second transition metal complex with a base.

In a further embodiment, the terminal alkyne is an alpha, omega-dialkyne.

In a further embodiment, the transition metal complex comprises a Group VI transition metal.

In a further embodiment, the Group VI transition metal is Mo or W.

In a further embodiment, the Group VI transition metal is Mo.

In a further embodiment, the first transition metal complex has the formula $X_3MX'$, wherein X is independently for each occurrence a σ-bonded ligand; M is a Group VI metal; and X' is chloride, bromide or iodide.

In a further embodiment, the first transition metal complex has the formula $X_3MX'$, wherein X is independently for each occurrence —$N(R)_2$, and R is independently for each occurrence H, alkyl, aryl, aralkyl, cycloalkyl, bicycloalkyl, or tricycloalkyl.

In a further embodiment, the first transition metal complex has the formula $X_3MX'$, wherein X is —N(i-Pr)(3,5-$Me_2C_6H_3$).

In a further embodiment, the first transition metal complex has the formula $X_3MX'$, wherein X' is I.

In a further embodiment, the first transition metal complex has the formula $X_3MX'$, wherein X is —N(i-Pr)(3,5-$Me_2C_6H_3$), M is Mo, and X' is I.

In another embodiment, the present invention relates to a method of preparing an enediyne or an alkyne metathesis catalyst or both, comprising the step of reacting an alkyne with an enedialkylidyne complex, thereby forming an enediyne or an alkyne metathesis catalyst or both.

In a further embodiment, the enedialkylidyne complex comprises a Group VI transition metal.

In a further embodiment, the enedialkylidyne complex comprises Mo or W.

In a further embodiment, the enedialkylidyne complex comprises Mo.

In a further embodiment, the enedialkylidyne complex has formula I or II:

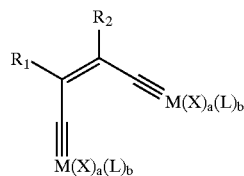

I

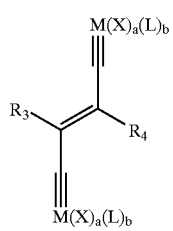

II wherein, independently for each occurrence:
M is a Group V, VI, VII, or VIII transition metal;
X is a σ-bonded ligand:
L is a donor bonded ligand;
$R_1$, $R_2$, $R_3$, and $R_4$ are H, or optionally substituted alkyl, aryl, and aralkyl; or $R_1$ and $R_2$ are covalently bonded to each other to form a 4–20 membered ring;
a is an integer from 1 to 3 inclusive; and
b is an integer from 0 to 4 inclusive.

In a further embodiment, the enedialkylidyne complex has formula III:

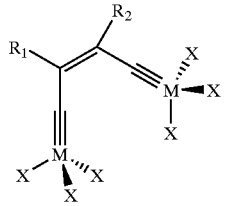

III wherein, independently for each occurrence:
X is a σ-bond ligand;
M is a Group VI transition metal; and
$R_1$ and $R_2$ are H, or optionally substituted alkyl, aryl, and aralkyl; or $R_1$ and $R_2$ are covalently bonded to each other to form a 4–20 membered ring.

In a further embodiment, the enedialkylidyne complex is of formula III and the attendant definitions, wherein X is independently for each occurrence —OR, and R is independently for each occurrence alkyl, aryl, aralkyl, cycloalkyl, bicycloalkyl, or tricycloalkyl.

In a further embodiment, the enedialkylidyne complex is of formula III and the attendant definitions, wherein X is —OR and R is independently for each occurrence selected from the group consisting of 2-methylphenyl, 2-phenylphenyl, 2,6-diphenylphenyl, 1-adamantanyl, 2-trifluoromethyl-2-propyl, and t-butyl.

In a further embodiment, the enedialkylidyne complex is of formula III and the attendant definitions, wherein M is independently for each occurrence Mo or W.

In a further embodiment, the enedialkylidyne complex is of formula III and the attendant definitions, wherein M is Mo.

In a further embodiment, the enedialkylidyne complex is of formula III and the attendant definitions, wherein $R_1$ and $R_2$ form a six-membered ring.

In a further embodiment, the enedialkylidyne complex is of formula III and the attendant definitions, wherein X is —O-adamantantyl, M is Mo, and $R_1$ and $R_2$ form a six-membered ring.

In a further embodiment, the alkyne metathesis catalyst has formula IV:

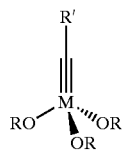

IV wherein
M is a Group VI transition metal;
R is independently for each occurrence H, alkyl, aryl, aralkyl, cycloalkyl, bicycloalkyl, or tricycloalkyl; and
R' is optionally substituted alkyl or optionally substituted aryl.

In a further embodiment, the alkyne metathesis catalyst is of formula IV and the attendant definitions, wherein M is Mo or W.

In a further embodiment, the alkyne metathesis catalyst is of formula IV and the attendant definitions, wherein M is Mo.

In a further embodiment, the alkyne metathesis catalyst is of formula IV and the attendant definitions, wherein R is independently for each occurrence selected from the group consisting of 2-methylphenyl, 2-phenylphenyl, 2,6-diphenylphenyl, 1-adamantanyl, 2-trifluoromethyl-2-propyl, and t-butyl.

In a further embodiment, the alkyne metathesis catalyst is of formula IV and the attendant definitions, wherein M is Mo, and R is independently for each occurrence selected from the group consisting of 2-methylphenyl, 2-phenylphenyl, 2,6-diphenylphenyl, 1-adamantanyl, 2-trifluoromethyl-2-propyl, and t-butyl.

In another embodiment, the present invention relates to a method of catalyzing an alkyne metathesis reaction, comprising combining an alkyne with an enedialkylidyne represented by formula V or VI:

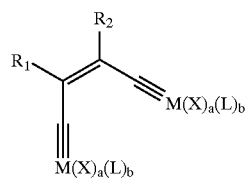

V

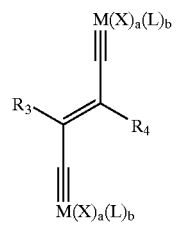

VI wherein, independently for each occurrence:
M is a Group V, VI, VII, or VIII transition metal;
X is a σ-bonded ligand:
L is a donor bonded ligand;

$R_1$, $R_2$, $R_3$, and $R_4$ are H, or optionally substituted alkyl, aryl, and aralkyl; or $R_1$ and $R_2$ are covalently bonded to each other to form a 4–20 membered ring;

a is an integer from 1 to 3 inclusive; and b is an integer from 0 to 4 inclusive.

In a further embodiment, the enedialkylidyne complex has formula VII:

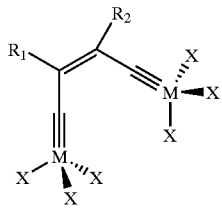

VII wherein, independently for each occurrence:

X is —OR;

R is alkyl, aryl, aralkyl, cycloalkyl, bicycloalkyl, or tricycloalkyl;

M is a Group VI transition metal; and $R_1$ and $R_2$ are H, or optionally substituted alkyl, aryl, and aralkyl; or $R_1$ and $R_2$ are covalently bonded to each other to form a 4–20 membered ring.

In a further embodiment, the enedialkylidyne complex is of formula VII and the attendant definitions, wherein R is independently for each occurrence selected from the group consisting of 2-methylphenyl, 2-phenylphenyl, 2,6-diphenylphenyl, 1-adamantanyl, 2-trifluoromethyl-2-propyl, and t-butyl.

In a further embodiment, the enedialkylidyne complex is of formula VII and the attendant definitions, wherein M is independently for each occurrence Mo or W.

In a further embodiment, the enedialkylidyne complex is of formula VII and the attendant definitions, wherein M is Mo.

In a further embodiment, the enedialkylidyne complex is of formula VII and the attendant definitions, wherein R is independently for each occurrence selected from the group consisting of 2-methylphenyl, 2-phenylphenyl, 2,6-diphenylphenyl, 1-adamantanyl, 2-trifluoromethyl-2-propyl, and t-butyl; and M is Mo.

In another embodiment, the present invention relates to a method of activating an enedialkylidyne complex for metathesis, wherein the endedialkylidyne complex comprises at least one σ-bonded amine ligand, comprising reacting the enedialkylidine complex with an alcohol to form at least one σ-bonded alkoxy ligand.

In another embodiment, the present invention relates to an enedialkylidyne complex having formula VIII or IX:

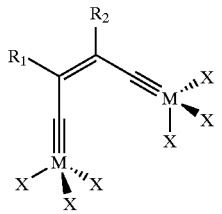

VIII

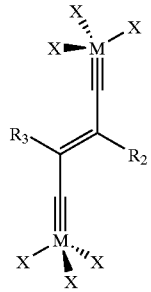

IX wherein, independently for each occurrence:

M is a Group VI transition metal;

X is a σ-bonded ligand;

$R_1$ and $R_2$ are H, or optionally substituted alkyl, aryl, and aralkyl; or $R_1$ and $R_2$ are covalently bonded to each other to form a 4–20 membered ring.

In a further embodiment, the present invention relates to a enedialkylidyne complex of formula VIII or IX and the attendant definitions, wherein M is a Mo or W.

In a further embodiment, the present invention relates to a enedialkylidyne complex of formula VIII or IX and the attendant definitions, wherein M is Mo.

In a further embodiment, the present invention relates to a enedialkylidyne complex of formula VIII or IX and the attendant definitions, wherein X is —OR, and R is independently for each occurrence alkyl, aryl, cycloalkyl, bicycloalkyl, or tricycloalkyl.

In a further embodiment, the present invention relates to a enedialkylidyne complex of formula VIII or IX and the attendant definitions, wherein X is —N(R)$_2$, and R is independently for each occurrence H, alkyl, aryl, cycloalkyl, bicycloalkyl, or tricycloalkyl.

In a further embodiment, the present invention relates to a enedialkylidyne complex of formula VIII or IX and the attendant definitions, wherein X is —N(i-Pr)(3,5-Me$_2$C$_6$H$_3$).

In a further embodiment, the present invention relates to a enedialkylidyne complex of formula VIII and the attendant definitions, wherein $R_1$ and $R_2$ are covalently bonded to each other to form a 4–20 membered ring.

In another embodiment, the present invention relates to the compound

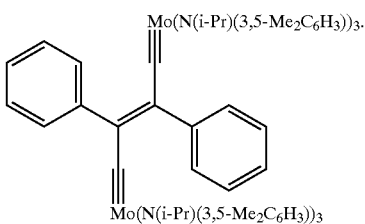

In another embodiment, the present invention relates to the compound

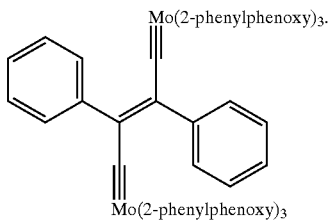

In another embodiment, the present invention relates to the compound

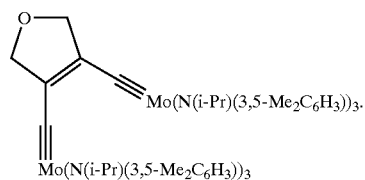

In another embodiment, the present invention relates to the compound

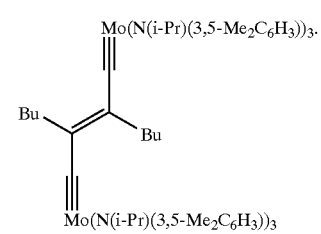

In another embodiment, the present invention relates to the compound

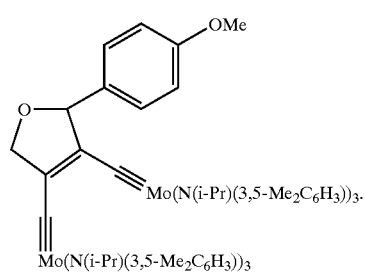

In another embodiment, the present invention relates to the compound

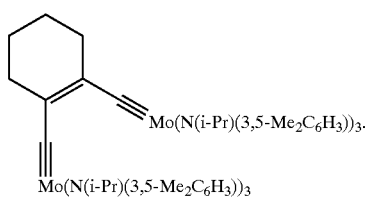

In another embodiment, the present invention relates to the compound

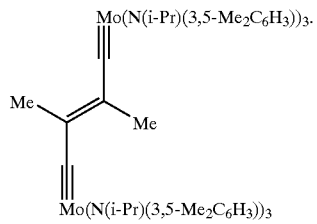

In another embodiment, the present invention relates to the compound

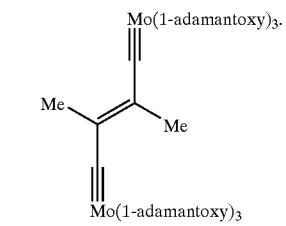

In another embodiment, the present invention relates to the compound

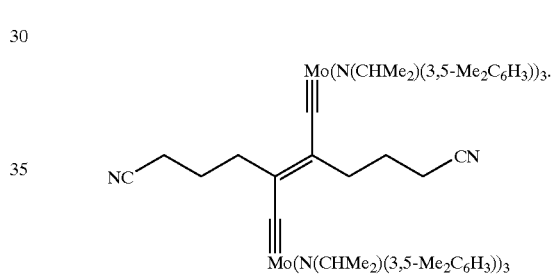

In another embodiment, the present invention relates to the compound

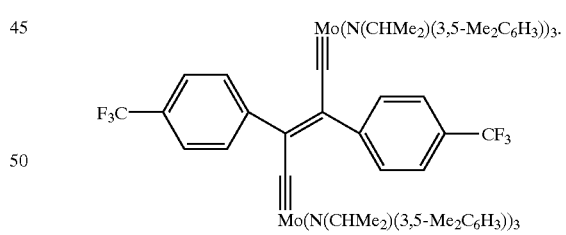

In another embodiment, the present invention relates to the compound

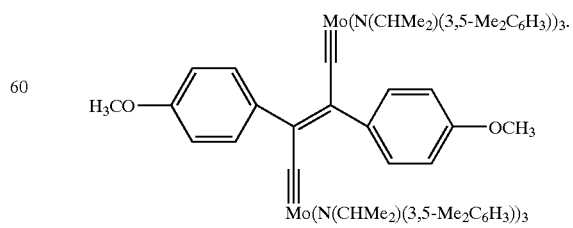

In another embodiment, the present invention relates to the compound

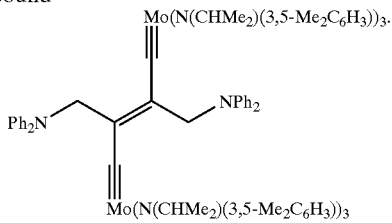

DETAILED DESCRIPTION OF THE INVENTION

Introduction

Figure 1:
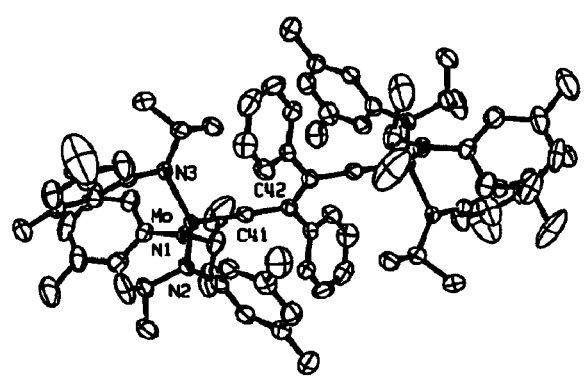
FIG. 1 depicts the ORTEP diagram of enedialkylidyne 3a showing thermal ellipsoids at the 50% probability level (symmetry equivalent atoms are not labeled). Selected bond lengths (Å): Mo-C41) 1.758(3); C41–C42) 1.443 (4); C42–C42A) 1.368(6). Selected angles (deg): Mo-C41–C42) 175.3(3).

Transition metal alkylidyne complexes are recognized as useful catalysts for the alkyne metathesis reaction. Schrock, R. R. *Chem. Rev.* 2002, 102, 145, and references therein. Recently, various transition metal recipes have been devised that effect this important transformation without the benefit of a well-defined active catalyst; this is particularly so in exciting polymer synthesis applications and impressive ring-closing variants utilized in natural product synthesis. Brizius, G.; Bunz, U. H. F. *Org. Lett.* 2002, 4, 2829. (b) Bunz, U. H. F. *Acc. Chem. Res.* 2001, 34, 998. (c) Ge, P.-H.; Fu, W.; Herrmann, W. A.; Herdtweck, E.; Campana, C.; Adams, R. D.; Bunz, U. H. F. *Angew. Chem., Int. Ed.* 2000, 39, 3607; Fürstner, A.; Mathes, C.; Lehmann, C. W. *Chem. Eur. J.* 2001, 7, 5299. (b) Fürstner, A.; Mathes, C. *Org. Lett.* 2001, 3, 221. (c) Grela, K.; Ignatowska, J. *Org. Lett.* 2002, 21, 3747. On the other hand, despite the fact that structurally well-defined traialkoxy-molybdenum alkylidyne complexes are known to function as efficient and functional-group-tolerant catalysts for alkyne metathesis, they have not been widely adopted because of difficulties encountered in their synthesis. McCullough, L. C.; Schrock, R. R.; Dewan, J. C.; Murdzek, J. C. *J. Am. Chem. Soc.* 1985, 107, 5987; Tsai, Y.-C.; Diaconescu, P. L.; Cummins, C. C. *Organometallics* 2000, 19, 5260. The present invention describes in one embodiment a convenient synthetic protocol for preparing such alkyne metathesis catalysts starting from Mo(H)(η²-Me₂CNAr)(N(i-Pr)Ar)₂, 1. Tsai, Y.-C.; Johnson, M. J. A.; Mindiola, D. J.; Cummins, C. C.; Klooster, W. T.; Koetzle, T. F. *J. Am. Chem. Soc.* 1999, 121, 10426. This protocol can also be directed toward the synthesis of conjugated (E)- and (Z)-ene-diynes, molecules of great importance in materials and biological chemistry owing respectively to their remarkable electronic and antibiotic properties. (a) Martin, R. E.; Gubler, U.; Cornil, J.; Balakina, M.; Boudon, C.; Bosshard, C.; Gisselbrecht, J.-P.; Diederich, F.; Günter, P.; Gross, M.; Brèdas, J.-L. *Chem. Eur. J.* 2000, 6, 3622. (b) Chow, S.-Y.; Palmer, G. J.; Bowles, D. M.; Anthony, J. E. *Org. Lett.* 2000, 2, 961; (a) Nicolaou, K. C.; Dai, W.-M. *Angew. Chem., Int. Ed. Engl* 1991, 30, 1387. (b) Danishefsky, S. J.; Shair, M. D. *J. Org. Chem.* 1996, 61, 16; (a) Nicolaou, K. C.; Ulven, T. M. T.; Baran, P. S.; Zhong, Y. L.; Sarabia, F. *J. Am. Chem. Soc.* 2002, 124, 5718. (b) Jones, G. B.; Wright, J. M.; Plourde, G. W., I; Hynd, G.; Huber, R. S.; Matthews, J. E. *J. Am. Chem. Soc.* 2000, 122, 1937. (c) Shimizu, T.; Miyasaka, D.; Kamigata, N. *Org Lett.* 2000, 2, 1923. (d) Hayashi, M.; Saigo, K. *Tetrahedron Lett.* 1997, 38, 6241. (e) Kosinski, C.; Hirsch, A.; Heinemann, F. W.; Hampel, F. *Eur. J. Org. Chem.* 2001, 3879; For a mechanistically distinct transition metal (Re, Mn) mediated synthesis of enediynes see: (a) Casey, C. P.; Kraft, S.; Powell, D. R. *J. Am. Chem. Soc.* 2002, 124, 2584. (b) Casey, C. P.; Dzwiniel, T. L. INDR 371 presented at ACS Meeting, Boston, Mass., August 2002.

Definitions

For convenience, certain terms employed in the specification, examples, and appended claims are collected here.

The articles "a" and "an" are used herein to refer to one or to more than one (i.e. to at least one) of the grammatical object of the article. By way of example, "an element" means one element or more than one element.

The term "σ-bonded ligand" refers to a ligand covalently bonded to a transition metal wherein the ligand oxidizes the transition metal. Non-limiting examples of σ-bonded ligands include —CH₃, —OH, —H, —NR₂, —OR, cyclopentadienyl, and the like.

The term "donor bonded ligand" refers to a ligand covalently bonded to a transition metal wherein the ligand does not oxidize the transition metal and donates at least one electron pair to the transition metal. Non-limiting examples of donor bonded ligands include :CO, :PR₃, :NR₃, and the like.

The term "enedialkyne" refers to a compound comprising an alkyne group at each end of a double bond. The double bond may be in the (Z) or (E) configuration and may be further substituted. The general formulas for an enedialkyne are as follows:

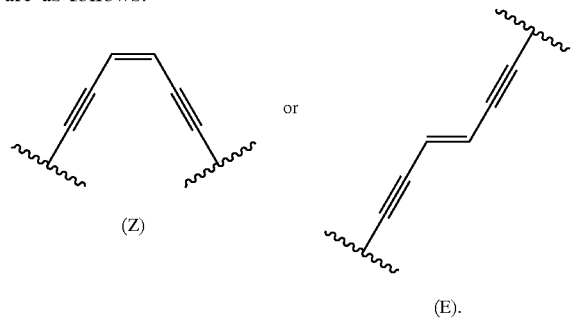

The term "enedialkylidyne" refers to two transistion metals bridged together via an enedialkyne moiety where the terminal carbons of the alkyne moieties are replaced by the transition metals. The double bond of the enedialkyne moiety may be in the (Z) or (E) configuration and may be further substituted. The tansition metal may have other ligands bonded to it as valency allows. The general formulas for an enedialkylidyne are as follows where M stands for a transition metal:

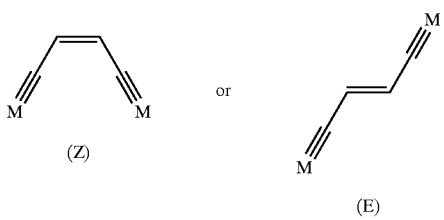

(Z)    or    (E)

The term "metathesis" refers to the act, process, or result of exchange, substitution, or replacement of atoms. Metathesis commonly refers to the exchange of atoms between two double bonded moieties or two triply bonded moieties. A non-limiting example of metathesis between an alkyne and a metal alkyne would proceed as follows:

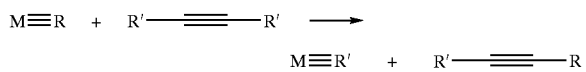

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

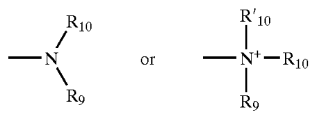

wherein $R_9$, $R_{10}$ and $R'_{10}$ each independently represent a group permitted by the rules of valence.

The term "acylamino" is art-recognized and refers to a moiety that can be represented by the general formula:

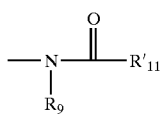

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

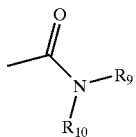

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

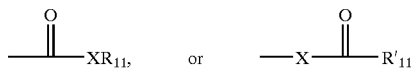

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo undesired transformation, such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986–87, inside cover.

Enedialkylidyne Compounds as Key Intermediates in Carbon-Carbon Double and Triple Bond Forming Processes The present invention establishes the potential of enedialkylidyne compounds for organic synthesis, and in particular for carbon-carbon bond forming reactions. Carbon-carbon double bond formation takes place as a consequence of terminal alkyne reductive coupling in the course of the novel synthesis of enedialkylidyne compounds, compounds which in turn can give rise subsequently to carbon-carbon triple bond formation via alkyne metathesis. The combination of terminal alkyne reductive coupling followed by alkyne metathesis represents a remarkable new synthetic methodology; one which can be applied to the synthesis of important classes of compounds including enediyne antitumor agents and alkyne metathesis catalysts.

In one embodiment, the convenient assembly of trans enedialkylidyne complexes is accomplished by treatment of a transition metal complex, for example, $X_3MI$ ($X=NR_2$= e.g., N(iso-Pr)(3,5-$C_6H_3Me_2$)) with terminal alkyne followed by base. Scheme 1.

Scheme 1

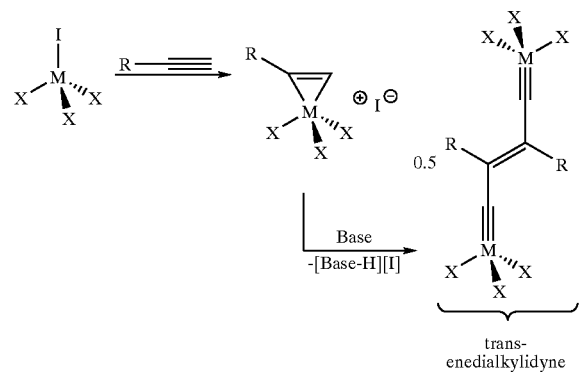

In another embodiment, an α,ω-diyne together with 2 equiv of a transition metal iodide yields, after treatment with base, the corresponding cis enedialkylidyne, illustrated below for the specific case of 1,7-octadiyne. Scheme 2.

Scheme 2

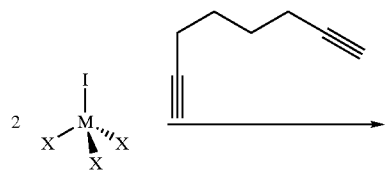

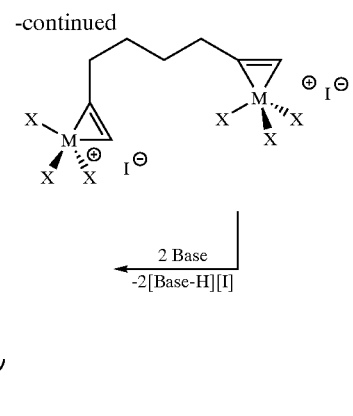

cis-enedialkylidyne

Generally, synthesis of enedialkylidyne complexes requires a 1:1 ratio of terminal alkyne to molybdenum complex, and an equivalent of base to effect dehydrohalogenation, providing a new C—C double bond (ene) and two molybdenum-carbon triple bonds (alkylidynes).

When the supporting ligand X is a nitrogen σ-bonded ligand, as in the synthesis of enedialkylidyne complexes with $X=NR_2$=e.g. N(iso-Pr)(3,5-$C_6H_3Me_2$), the M-C triple bonds are typically not active for alkyne metathesis. However, in general, the enedialkylidyne complexes may be activated for alkyne metathesis when the nitrogen σ-bonded ligands are replaced with oxygen σ-bonded ligands; the replacement is easily accomplished by treatment with an alcohol (ROH).

Scheme 3 depicts treatment of a cis-enedialkylidyne in which $X=NR_2$ is treated with 6 equiv of an alcohol to produce a new cis-enedialkylidyne in which X=OR. The liberated secondary amines, $HNR_2$, are readily separated from the reaction mixture; moreover, the transition metal-carbon bonds of the product are active for alkyne metathesis. Accordingly, subsequent treatment with an internal alkyne replaces the M—C triple bonds with C—C triple bonds, generating stoichiometrically an enediyne along with two equivalents of trialkoxy-M alkylidyne, which may be used in subsequent alkyne metathesis reactions.

Notably, both products of this transformation are extremely useful. The alkyne metathesis catalysts can be used in synthesis to prepare large-ring macrocycles, including variants of naturally occurring antibiotics. Further, the remarkable method for enediyne synthesis will open new avenues in medicinal chemistry because access to such compounds has been limited, notwithstanding the fact that they are promising antitumor agents.

Scheme 3

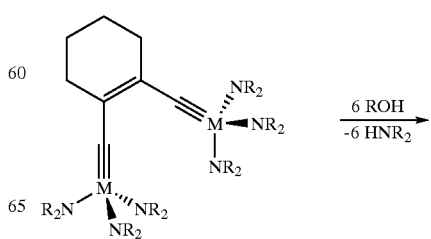

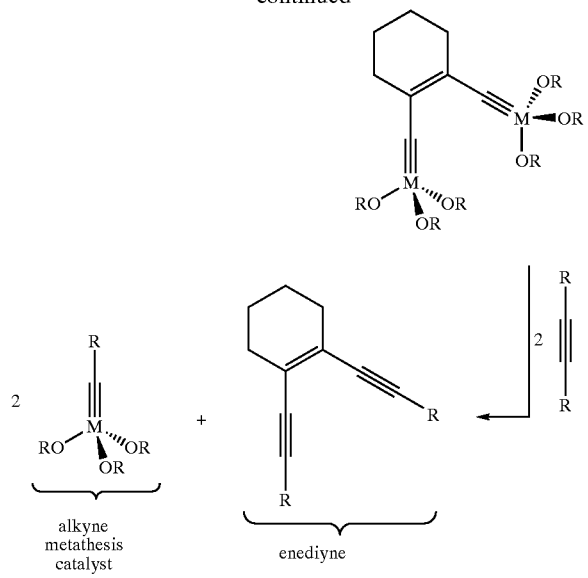

In general, the synthetic strategy illustrated here involves: (i) terminal alkyne coupling to give enedialkylidyne; (ii) activation for alkyne metathesis by replacement of NR$_2$ with OR ligands on molybdenum; and (iii) metathesis with an internal alkyne. Materials with carbon-carbon double and triple bonds are produced efficiently, as are well-defined catalysts for general application in alkyne metathesis. Throughout, R has been used in most generic terms; in other words, the methodology is expected to be general in scope and permissive of introduction of a variety of functional groups.

Molybdenum Enedialkylidyne Complexes and the Synthesis of Enedialkynes.

The above reaction schemes will now be exemplified for when the transition metal is the Group VI transition metal molybdenum. Molybdenum(VI) alkyne complexes 2a–g, prepared from molybdaziridine hydride 1 in high yield (Scheme 4), are converted to the dinuclear enedialkylidyne complexes 3a–g upon deprotonation with Li[N(SiMe$_3$)$_2$]. Schrock, R. R. *Chem. Rev.* 2002, 102, 145, and references therein; (a) Brizius, G.; Bunz, U. H. F. *Org. Lett.* 2002, 4, 2829. (b) Bunz, U. H. F. *Acc. Chem. Res.* 2001, 34, 998. (c) Ge, P.-H.; Fu, W.; Herrmann, W. A.; Herdtweck, E.; Campana, C.; Adams, R. D.; Bunz, U. H. F. *Angew. Chem., Int. Ed.* 2000, 39, 3607; (a) Fürstner, A.; Mathes, C.; Lehmann, C. W. *Chem. Eur. J.* 2001, 7, 5299. (b) Fürstner, A.; Mathes, C. *Org. Lett.* 2001, 3, 221. (c) Grela, K.; Ignatowska, *J. Org. Lett.* 2002, 21, 3747; McCullough, L. C.; Schrock, R. R.; Dewan, J. C.; Murdzek, J. C. *J. Am. Chem. Soc.* 1985, 107, 5987.

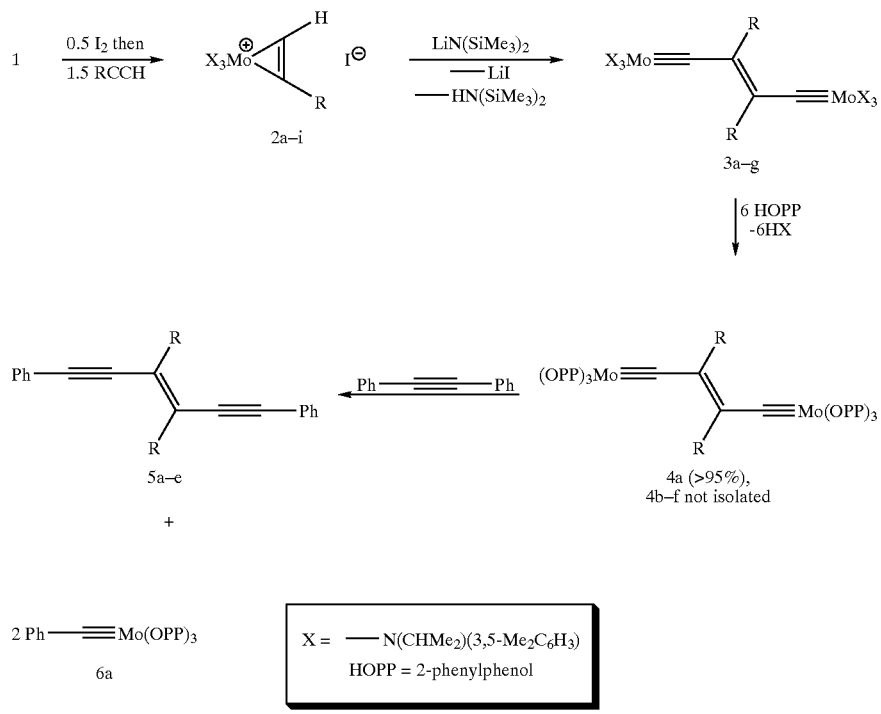

Yields of the various compounds prepared according to Scheme 4 are presented below in Table 1.

TABLE 1

Compound Yields.

| Entry | R | % Yields | | |
|---|---|---|---|---|
| | | 2 | 3 | 5 |
| a | Ph | 86% | 83% | 83% |
| b | Me | 74% | 97% | 81% |
| c | n-Bu | 79% | 85% | 69% |
| d | (CH$_2$)$_3$CN | 85% | 85% | 58% |
| e | 4-CF$_3$C$_6$H$_4$ | 83% | 68% | 77% |
| f | 4-CH$_3$C$_6$H$_4$ | 80% | 80% | — |
| g | CH$_2$NPh$_2$ | 82% | 60% | — |
| h | t-Bu | 57% | —[a] | — |
| i | SiMe$_3$ | 78% | —[a] | — |

[a]Dimerization not observed from X$_3$MoCC—R. Deprotonation leads to formation of the corresponding triamidomolybdenum(IV) acetylide. The phenylacetylide complex formed from 2a has been isolated and characterized by X-ray crystallography. See also: Shih, K.-Y.; Schrock, R. R.; Kempe, R. J. Am. Chem. Soc. 1994, 116, 8804.

Reaction times for these reductive coupling reactions proceeding via molybdenum(IV) acetylides vary from 96 h (R=Ph) to less than 2 h (R=Me). The enedialkylidyne 3f derived from 4-methoxyphenyl acetylene is formed in high yield in 12 h, demonstrating that the coupling reaction occurs more readily for electron-rich phenylacetylenes. However, complexes 2h and 2i derived from tert-butyl acetylene and trimethylsilyl acetylene do not provide dimeric enedialkylidynes under these reaction conditions; instead, the monomeric molybdenum(IV) acetylides so derived are isolable. Deprotonation leads to formation of the corresponding triamidomolybdenum(IV) acetylide. The phenylacetylide complex formed from 2a has been isolated and characterized by X-ray crystallography; its reactivity will be the subject of a forthcoming paper. See also: Shih, K.-Y.; Schrock, R. R.; Kempe, R. J. Am. Chem. Soc. 1994, 116, 8804. An X-ray crystal structure of 3a established the E-disposition of the two alkylidyne fragments as shown in FIG. 1. Both the Mo—C bond distance (1.758(3) Å) and the Mo—C—C bond angle (175.3(3)°) of the crystallographically identical alkylidyne units are parameters typical of other structurally characterized triamidomolybdenum alkylidyne compounds. Cochran, F. V.; Schrock, R. R. Organometallics 2001, 20, 2127. In all cases, characteristic resonances for the alkylidyne CR carbons (293–302 ppm) were observed by $^{13}$C NMR spectroscopy.

The enedialkylidynes 3a–e are conveniently elaborated to the corresponding enediynes 5a–e via a two-step, one-pot protocol involving replacement of the electron-rich amido ligands with 2-phenylphenoxy (OPP) ligands followed by treatment with diphenylacetylene. This protocol takes advantage of the well-established reactivity of trialkoxymolybdenum alkylidynes with alkynes; notably, the electronically saturated triamido derivatives, 3, exhibit no reactivity with diphenylacetylene. McCullough, L. C.; Schrock, R. R.; Dewan, J. C.; Murdzek, J. C. J. Am. Chem. Soc. 1985, 107, 5987; Tsai, Y.-C.; Diaconescu, P. L.; Cummins, C. C. Organometallics 2000, 19, 5260.

The aryloxy-substituted enedialkylidyne 4a (R=Ph) is easy to isolate owing to its low solubility in diethyl ether. It is converted to enediynes 5aa, 5ab, and 5ac when treated with the appropriate symmetrical alkyne as shown in eq 1. In the case of the 4a to 5aa conversion, the benzylidyne coproduct, 6a, could be isolated in 45% yield and was demonstrated to exhibit alkyne metathesis activity. For instance 6a catalyzes the conversion of 1-phenylpropyne to diphenylacetylene (and 2-butyne) at 24° C. as shown in eq 2. The protocol consists of mixing 1-phenylpropyne with catalytic alkylidyne (1–2 mol % Mo) in toluene and removing the solvent slowly (1–2 h) in vacuo (rough pump) with concomitant removal of 2-butyne.

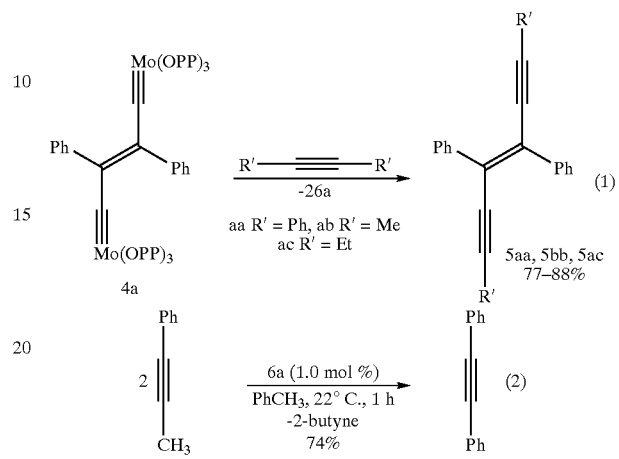

However, enedialkylidyne 4a (isolated in >95% yield from 3a) can itself serve as an efficient alkyne metathesis precatalyst as illustrated by the examples in eq 3. Hence, a robust and highly effective alkyne metathesis initiator, 4a, is prepared in three high-yielding steps (68% overall) from the readily procured molybdaziridine hydride, 1. This source of a reactive triamidomolybdenum(III) synthetic equivalent is typically prepared in 10–20 g quantities as a crystalline solid (Et$_2$O) starting from MoCl$_3$(thf)$_3$, which is prepared from MoCl$_5$ via Poli's procedure, see: Stoffelbach, F.; Saurenz, D.; Poli, R. Eur. J. Inorg. Chem. 2001, 10, 2699. Enedialkylidyne 4a and its two direct synthetic precursors 2a and 3a all are conveniently isolated as powders in high yields owing to their insolubility in pentane or diethyl ether.

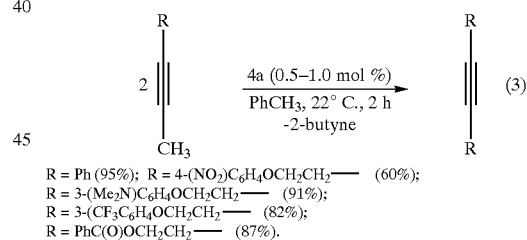

R = Ph (95%); R = 4-(NO$_2$)C$_6$H$_4$OCH$_2$CH$_2$— (60%);
R = 3-(Me$_2$N)C$_6$H$_4$OCH$_2$CH$_2$— (91%);
R = 3-(CF$_3$C$_6$H$_4$OCH$_2$CH$_2$— (82%);
R = PhC(O)OCH$_2$CH$_2$— (87%).

A powerful intramolecular reductive coupling protocol has been adapted from the above-described chemistry, providing conjugated cycloalkenedialkylidynes. The corresponding cycloalkenediynes (Scheme 5) can be obtained by using the combined alcoholysis/alkyne metathesis strategy described earlier. The pentane insoluble diyne complexes 7 are prepared in high yield and converted to the enedialkylidynes 8 by dropwise addition of a tetrahydrofuran (thf) solution of 7 to 2 equiv of Li[N(SiMe$_3$)$_2$] dissolved in thf. Intramolecular coupling occurs rapidly, and purification consists of removing the thf in vacuo, replacing with pentane, and filtering twice through Celite. The enedialkylidyne products are then redissolved in pentane with a few drops of thf and stored at −35° C., leading to precipitation of a solid. After isolation by filtration, the enedialkylidyne is purified further by crystallization from a yellow-orange pentane/thf solution. Yields for the yellow crystalline solids range from 38% for 8c to 68% for 8d.

Scheme 5

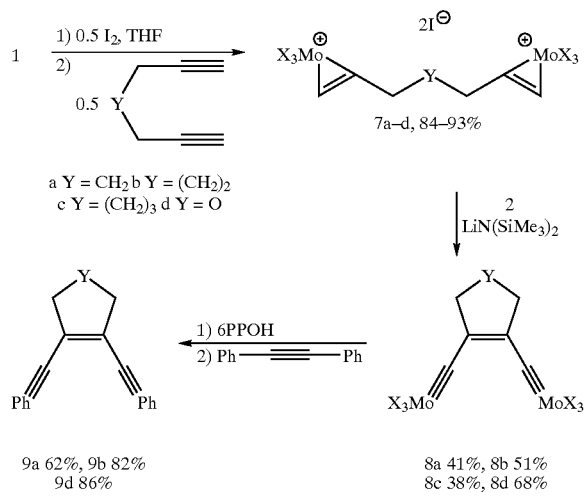

a Y = CH₂ b Y = (CH₂)₂
c Y = (CH₂)₃ d Y = O 9a 62%, 9b 82%
9d 86%

8a 41%, 8b 51%
8c 38%, 8d 68%

¹H NMR analysis of the crude reaction mixture for 8c confirms that cyclization proceeds less cleanly than is observed for the other derivatives, likely reflective of the increased steric demands in placing two bulky alkylidyne fragments adjacent on a cycloheptene ring. ¹³C NMR spectroscopy shows one signal in each case that is typical for the Cα resonance of a molybdenum alkylidyne complex (290–302 ppm). The cycloalkenedialkylidyne complexes 8 were subsequently converted to enediynes 9 using the tandem alcoholysis/alkyne metathesis strategy delineated above. No attempts in this case were made to isolate alkylidyne 6a.

Figure 2:
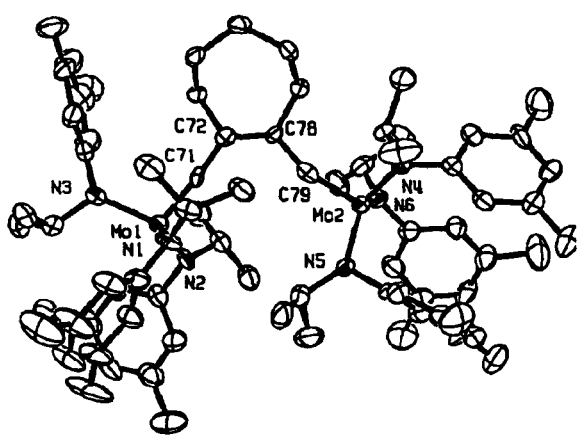
FIG. 2 depicts the ORTEP diagram of enedialkylidyne 8c showing thermal ellipsoids at the 50% probability level. Selected bond lengths (Å): Mo1-C71) 1.752(7); Mo2-C79) 1.754(7); C71–C72) 1.433(9); C78–C79) 1.461(9). Selected angles (deg): Mo1-C71–C72) 176.0(5); Mo2-C79–C78) 161.2(5).

X-ray structure determinations of complexes 8c (X=(CH₂)₃) and 8d (X=O) illustrate the steric pressure inflicted on the two alkylidyne fragments vicinally disposed on a cycloalkene ring; see FIG. 2. In the case of 8d, accommodation of these two bulky groups is facilitated by distortion from linearity of both of the Mo—C—C angles (167.1(6)° and 173.6(6)°); no significant difference, however, is observed in the two Mo—C bond lengths (1.747(8) and 1.760(7) Å, respectively). For the cycloheptenedialkylidyne 8c, steric pressure is expected to be even greater, and in the solid state, one of the Mo—C—C angles is significantly bent (161.2(5)°) while the other is only slightly kinked (176.0(5)°). Again, both Mo—C bond distances are comparable (1.754(7) and 1.752(7) Å, respectively).

EXEMPLIFICATION

The invention now being generally described, it will be more readily understood by reference to the following examples, which are included merely for purposes of illustration of certain aspects and embodiments of the present invention, and are not intended to limit the invention.

Example 1
Synthesis of [(3,5-Me₂C₆H₄[i-Pr]N)₃Mo(H-CC-Ph)]⁺[I]⁻

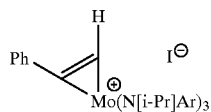

To molybdaziridine hydride (3.70 g, 6.35 mmol) (Tsai, Y.-C. et al. J. Am. Chem. Soc. 1999, 121, 10426–27) dissolved in pentane (20 mL) was added I₂ (1/2 eq, 806 mg, 3.175 mmol) dissolved in Et₂O (10 mL in 2 portions). The initially dark brown solution becomes dark green in color over thirty minutes. Phenylacetylene (960 mg, 9.5 mmol) dissolved in pentane (5 mL) was then added by pipette leading to formation of a dark precipitate suspended in dark brown supernatant. After 1 h, the reaction mixture was filtered through a frit and washed thoroughly with pentane until the resulting filtrate was colorless. The yellow solid on the frit was dried in vacuo and isolated in 86% yield (4.40 g, 5.46 mmol).

Example 2
Synthesis of (E)-1,2-((3,5-Me₂C₆H₄[i-Pr]N)₃MoC)₂-stilbene

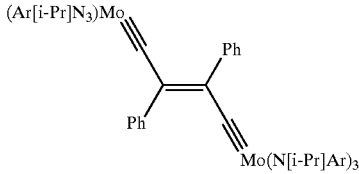

Lithium hexamethyldisilazide (LiHMDS, 334 mg, 2.0 mmol) dissolved in 2 mL tetrahydrofuran (THF) was added via pipette to 1.62 g of [(3,5-Me₂C₆H₄[i-Pr]N)₃Mo(H-CC-Ph)]⁺[I]⁻ (2.0 mmol) dissolved in 1 mL of THF. After 72 h, the reaction mixture was concentrated to a dark oil. The mixture was filtered through a Celite-packed frit using pentane. The Celite was then washed with toluene until yellow-orange color completely washed through. The filtrate was concentrated to a dark solid then filtered through a frit using pentane. The yellow solid on the frit was washed with pentane until the resulting filtrate was light yellow (initially, it is dark brown). This yellow-orange solid was dried in vacuo providing the enedialkylidyne in 74% yield (1.10 g). ¹H NMR (C₆D₆, 400 MHz): δ 7.78 (d, J=7.5 Hz, 4 Hz), 7.41 (t, J=7.5 Hz, 4H), 7.22 (t, J=7.3 Hz), 6.61 (s, 6H), 6.57 (s, 12H), 3.94 (sept, J=6.4 Hz), 2.16 (s, 36H), 1.10 (d, J=6.4 Hz). ¹³C NMR (C₆D₆, 100 MHz): δ 296.5, 150.9, 146.4, 140.9, 137.6, 131.3, 127.5, 127.1, 126.6, 61.8, 25.0, 21.8 (one C missing).

Example 3
Synthesis of (E)-1,2-((2-phenylphenoxy)₃MoC)₂-stilbene-2 [THF]

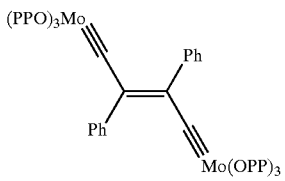

1.0 g (0.67 mmol) of the enedialkylidyne prepared above was partially dissolved in 5 mL of Et₂O. 685 mg (4.0 mmol) of 2-phenylphenol dissolved in 5 mL of Et₂O was then added producing a dark red solution. After a few minutes, a yellow solid begins to precipitate. After 2 hours, stirring was stopped and the precipitate was allowed to settle. The supernatant was carefully removed by pipette, more Et₂O was added then removed by pipette. This process was repeated two more times then the solid was dried in vacuo. 720 mg of a yellow solid was isolated, ¹H NMR analysis showing there still to be isopropylaniline ligand present. The solid was washed with pentane on a frit yielding 566 mg (60%). ¹H NMR (400 MHz, C₆D₆): δ 7.33–7.26 (m, 18H), 7.20 (td, 6H), 7.15–7.02 (m, 30H), 6.68 (t, 2H), 6.53 (t, 4H), 6.12 (d, 4H), 3.28 (m, 8H, THF), 1.10 (m, 8H, THF).

Notably, this type of dimeric OPP enedialkylidyne compound, which is relatively easy to isolate, may be used as an alkyne metathesis catalyst.

Example 4
Synthesis of (E)-1,2-bis-phenylethynylstilbene (three-step procedure)

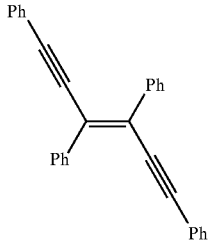

To 811 mg (1 mmol) of the alkyne complex prepared above dissolved in 5 mL THF was added LiHMDS (167 mg, 1 mmol) dissolved in 5 mL of THF. The reaction mixture was stirred for 72 hours, then concentrated and filtered through Celite using pentane then toluene. The filtrate was concentrated and transferred using 10 mL of toluene to a 20 mL vial. 510 mg (3.0 mmol) of 2-phenylphenol dissolved in 2 mL of toluene was added. After 1 hour, 534 mg (3.0 mmol) of diphenylacetylene dissolved in 1 mL of toluene was added. After 2 hours, H$_2$O was added, extracted several times with EtOAc, dried using MgSO$_4$, filtered then concentrated. Purification by column chromatography provided 232 mg (61%) of the enediyne as a white solid. $^1$H NMR (400 MHz, CDCl$_3$): δ 8.02–7.98 (m, 4H), 7.53–7.46 (m, 4H), 7.44–7.38 (m, 2H), 7.34–7.28 (m, 10H); $^{13}$C NMR (100 MHz, CDCl$_3$): δ 139.0, 131.4, 129.2, 128.6, 128.5, 128.3, 128.3, 127.8, 123.2, 98.5, 90.9.

Example 5
Synthesis of (E)-1,2-bis-phenylethynylstilbene (two-step procedure)

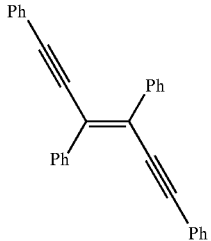

To 490 mg (0.35 mmol) of (E)-1,2-((3,5-Me$_2$C$_6$H$_4$[i-Pr]N)$_3$MoC)$_2$-stilbene dissolved in 10 mL of toluene was added 357 mg (2.1 mmol) of 2-phenylphenol as a solid. After 1 hour, 374 mg, 2.1 mmol) of diphenylacetylene was added dissolved in 2 mL of toluene. The reaction mixture was stirred for 16 hours then 1M HCl was added. The 2-phase mixture was diluted with EtOAc and the layers separated. The aqueous layer was extracted several times with EtOAc then dried using MgSO$_4$ and filtered. 2–3 g of silica gel was added to the solution which was then concentrated to a solid. Purification by column chromatography (silica, hexanes then 2% EtOAc/hexanes as eluent) afforded 103 mg (77%) of the enediyne as a white solid, spectral data as above.

Example 6
Synthesis of (E)- and (Z)-1,2-bis-(1-butynyl)-stilbene (6.8:1 E:Z) (One-step Procedure)

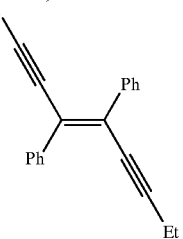

310 mg (0.20 mmol) of enedialkylidyne, (E-)-1,2-((2-phenylphenoxy)$_3$MOC)$_2$-stilbene was dissolved in 2 mL of toluene. 99 mg (1.20 mmol) of 3-hexyne dissolved in 1 mL of toluene was added. After 1 hour, H$_2$O was added to the reaction mixture and then extracted several times with EtOAc. Purification by column chromatography led to the isolation of a mixture of (E)- and (Z)-enediynes as a white solid (50 mg, 88%). $^1$H NMR (400 MHz, C$_6$D$_6$): (E)-isomer, δ 8.18 (d, 4H), 7.23 (t, 4H), 7.11 (t, 2H), 1.94 (q, 4H), 0.79 (t, 6H); (Z)-isomer, δ 7.37 (m, 4H), 6.93–6.85 (m, 6H), 2.22 (t, 4H), 1.02 (t, 6H). $^{13}$C NMR (100 MHz, C$_6$D$_6$): (E)-isomer, δ 141.0, 130.0, 128.5, 128.3, 127.9, 101.1, 82.2, 14.2, 13.7; (Z)-isomer, δ 139.5, 130.5, 129.3, 98.9, 83.7, 14.6, 14.3.

Example 7
Synthesis of the alkyne metathesis catalyst, benzylidne complex, (2-phenylphenoxy)$_3$MoC-Ph2THF

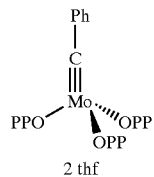

2 thf

To (E)-1,2-((2-phenylphenoxy)$_3$MoC)$_2$-stilbene 500 mg (0.33 mmol) suspended in 2 mL of Et$_2$O was added 178 mg (1.0 mmol) of diphenylacetylene leading to dissolution of the solids. Over the next several hours, a red solid precipitates form the solution which was collected by filtration (228 mg) and washed with pentane. The solid was suspended in pentane and a few drops of THF were added until completely dissolved and then the mixture was stored in the freezer. 118 mg (21%) of a red crystalline material was isolated (with 2 THF molecules). $^1$H NMR (400 MHz, C$_6$D$_6$): δ 7.65 (d, 6H), 7.29 (d, 3H), 7.21 (t, 6H), 7.09 (m, 3H), 6.95 (t, 3H), 6.86 (t, 3H), 6.68 (m, 5H), 6.52 (d, 1H), 6.15 (d, 2H), 3.70–3.55 (m, 8H, THF), 1.38–1.28 (m, 8H, THF). $^{13}$C NMR (100 MHz, C$_6$D$_6$): δ 292.4, 169.1, 143.3, 140.5, 130.9, 130.7, 130.3, 130.2, 129.1, 128.5, 128.3, 127.4, 127.3, 122.6, 121.8, 69.3, 26.0.

Example 8
Synthesis of [(((3,5-Me$_2$C$_6$H$_4$[i-Pr]N)$_3$Mo)$_2$(HCCCH$_2$OCH$_2$CCH)]$^{2+}$[I$_2$]$^{2-}$

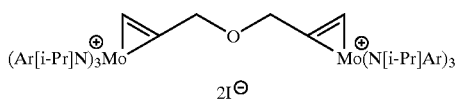

To 2.33 g (4.0 mmol) of molybdaziridine hydride dissolved in 20.0 mL of THF was added 508 mg (2.0 mmol) of I$_2$ dissolved in 10.0 mL of THF. The resulting dark green solution was stirred for 30 min then 179 mg (1.90 mmol) of propargyl ether dissolved in 3 mL of THF was added via pipette. The dark green color changes to green-brown then brown over the period of an hour. The solution was then concentrated in vacuo to a dark brown/black oily solid.

Pentane was added then removed in vacuo providing a brown powder. The brown solid was collected on a frit and washed thoroughly with pentane until fthe filtrate was colorless. The solid was then washed with approximately 10 mL of Et$_2$O and then dried in vacuo. 2.33 g (81% based on propargyl ether) of a yellow brown solid was isolated. $^1$H NMR (300 MHz, C$_6$D$_6$): δ 12.60 (s, 1H), 6.77 (s, 12H), 6.68 (s, 4H), 6.62 (s, 6H), 4.54 (m, 6H), 2.27 (s, 36H), 0.89 (d, 36H).

Example 9
Synthesis of 3,4-((3,5-Me$_2$C$_6$H$_4$[i-Pr]N)$_3$MoC)$_2$-2,5-dihydrofuran

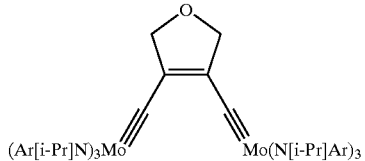

3.60 g (2.17 mmol) of the diyne complex prepared above was dissolved in 15.0 mL of THF and added dropwise by pipette (20 minute addition) to a vigorously stirred solution of LiHMDS (725 mg, 4.34 mmol) in 100.0 mL of THF. After 1 h, solvent was removed in vacuo; pentane was added to the dark brown oily solid and then filtered through a frit packed with Celite. Continued washing with pentane was carried out until the new filtrate was colorless. The filtrate was then concentrated to an oily brown solid and then transferred to a 100 mL round bottom flask using 60 mL of pentane then concentrated in vacuo to approximately 40 mL (to a point where solid begins to precipitate). The flask was then stored in −35° C. freezer overnight. The mixture was then filtered through a frit and the solid collected was washed with pentane providing 1.35 g (44.5%) of a yellow solid. $^1$H NMR showed product to be clean and contained two THF molecules. $^1$H NMR (C$_6$D$_6$): 6.72 (s, 6H), 6.58 (s, 12H), 4.76 (sept., J=6.4 Hz, 6H), 4.11 (s, 4H), 2.10 (s, 36H), 1.46 (d, J=6.4 Hz, 36H).

Example 10
Synthesis of 3,4-bis-phenylethynyl-2,5-dihydrofuran (two-step procedure)

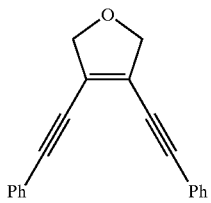

350 mg (0.25 mmol) of the enedialkylidyne, the preparation of which is described above, was dissolved in 5.0 mL of toluene. 255 mg (1.50 mmol) of 2-phenylphenol dissolved in 5.0 mL of toluene was added; the solution changes from brown to deep red in color. After 90 min, 267 mg (1.50 mmol) of diphenylacetylene was added as a solid all at once. The solution retains a deep red color. After 90 min, the reaction mixture was diluted with 20 mL of 1M HCl(aq) and then diluted with EtOAc. The layers were separated and then the organic layer was washed three times with 1M HCl. The combined HCl layers were washed once with EtOAc and then the combined organic layers were washed with brine and dried using MgSO$_4$ then filtered. To the filtrate was added 2 or 3 g of silica gel, concentrated by rotovap to a powder then loaded onto silica-packed column (hexane). Elution using hexane then 1% EtOAc/hexane then 5% EtOAc/hexane enabled isolation of the enediyne in 86% yield (58 mg, 0.215 mmol) as a white solid. $^1$H NMR (400 MHz, CDCl$_3$): δ 7.55–7.52 (m, 4H), 7.39–7.35 (m, 6H), 4.86 (s, 4H); $^{13}$C NMR (100 MHz, CDCl$_3$): 131.7, 128.9, 128.4, 125.6, 122.6, 99.0, 81.3, 77.4.

Example 11
Synthesis of 3,4-bis-phenylethynyl-2,5-dihydrofuran (three-step procedure)

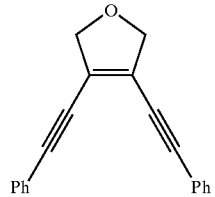

1.04 g (0.63 mmol) of the diyne complex was dissolved in 5 mL of THF and added by pipette dropwise to LiHMDS (210 mg, 1.26 mmol) dissolved in 20 mL of THF. After 45 minutes, the reaction mixture was concentrated to a dark brown oil. Pentane was added and the mixture was filtered through Celite. The filtrate was transferred to a 100 mL round bottom flask, concentrated and dissolved in 10 mL of toluene. 640 mg (3.76 mmol) of 2-phenylphenol dissolved in 5 mL of toluene was added, the color of the solution changes from green-brown to deep red. After 1 h, 670 mg (3.76 mmol) of diphenylacetylene was added. After 1 h, 1M HCl was added and after typical work-up and column chromatography, 51 mg (30%) of the enediyne was isolated as a pale yellow solid, see spectral data above.

Example 12
Synthesis of alkyne complex, [(3,5-Me$_2$C$_6$H$_4$[i-Pr]N)$_3$Mo)(1-hexyne)]$^+$[I]$^-$

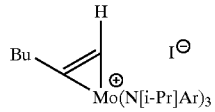

1.16 g (2.0 mmol) of molybdaziridine hydride was dissolved in 3 mL of pentane. 254 mg (1.0 mmol) of I$_2$ dissolved in 3 mL of Et$_2$O was added producing a dark green solution. After 30 minutes, 246 mg (3 mmol) of 1-hexyne dissolved in 2 mL of pentane was added leading to color change from green to brown and precipitation of a brown solid. After 30 minutes, the reaction mixture was filtered through a frit and washed thoroughly with pentane until resulting filtrate was colorless. 1.25 g (79%) of a yellow-orange solid was isolated. $^1$H NMR (C$_6$D$_6$): δ10.80 (s, 1H), 6.88 (s, 6H), 6.60 (s, 3H), 5.05 (m, 3H), 3.15 (t, 2H), 2.28 (s, 18H), 1.58 (m, 2H), 1.44 (m, 2H), 1.12 (s, 18H), 0.88 (t, 3H).

Example 13
Synthesis of (E)-((3,5-Me$_2$C$_6$H$_4$[i-Pr]N)$_3$MoC)$_2$-5-decyne

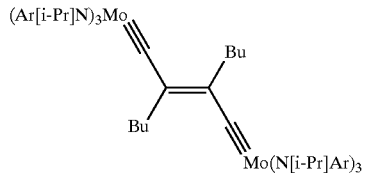

1.25 g (1.58 mmol) of the alkyne complex prepared directly above was suspended in 3 mL of C$_6$H$_6$. 264 mg (1.58 mmol) of LiHMDS dissolved in 3 mL of C$_6$H$_6$ was added leading to a dark brown mixture with a dark precipitate. After 15 minutes, the mixture was filtered through Celite packed pipette into a 20 mL vial. After 16 hours, the reaction mixture was concentrated in vacuo to provide a yellow-green solid. The solid was dissolved in pentane and stored in the freezer. Two recrystallizations provided 890 mg (85%) of a yellow-green crystalline solid. $^1$H NMR (400 MHz, $C_6D_6$): δ 6.79 (s, 12H), 6.64 (s, 6H), 4.51 (m, 6H), 2.30–2.15 (m, 4H), 2.20 (s, 36H), 1.70–1.58 (m, 4H), 1.50–1.35 (m, 4H), 1.35 (d, J=6.6 Hz), 1.16 (t, J=7.2 Hz, 6H); $^{13}$C NMR (100 MHz, $C_6D_6$): δ 301.7, 152.3, 148.2, 137.7, 127.0, 126.4, 61.6, 34.4, 33.5, 25.1, 24.9, 21.9, 15.4.

Example 14
Synthesis of enediynes (E)- and (Z)-bis-(1-butynyl)-5-decyne (three-step procedure)

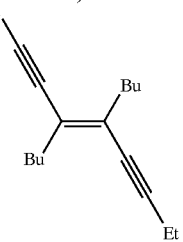

To a reddish-brown solution of 1.07 g (1.35 mmol) of the alkyne adduct above dissolved in 10 mL of THF was added LiHMDS (225 mg, 1.35 mmol) dissolved in 5 mL of THF. The solution was stirred for 14 hours, concentrated and filtered through Celite using pentane. The filtrate was transferred to a 100 mL round-bottom flask using $Et_2O$ then concentrated. The mixture was dissolved in 5 mL of toluene and 2-phenylphenol (689 mg, 4.05 mmol) dissolved in 3 mL of toluene was added. After 1 hour, 3-hexyne (4.05 mmol) dissolved in 2 mL of toluene was added. After 2 hours, 1M HCl was added. Following typical work-up and purification by column chromatography, 122 mg (74%) of a mixture of (E)- and (Z)-enediynes was isolated as a pale yellow liquid.

Example 15
Synthesis of $[((3,5-Me_2C_6H_4[i-Pr]N)_3Mo)_2(HCCCH(p-MeOC_6H_4)OCH_2CCH)]^{2+}[I_2]^{2-}$

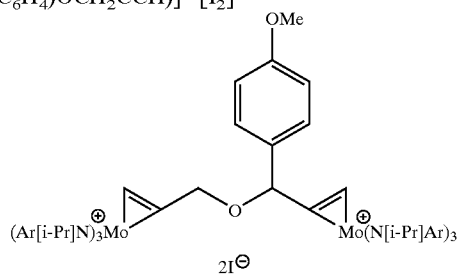

To 1.16 g (2.0 mmol) of molybdaziridine hydride dissolved in 5.0 mL of THF was added 254 mg (1.0 mmol) of $I_2$ dissolved in 5.0 mL of THF. The resulting dark green solution was stirred for 30 min then 180 mg (0.9 mmol) of 3-(p-MeOC$_6$H$_4$)propargyl ether dissolved in 2 mL of THF was added via pipette. The color of the solution changes from dark green to brown; after 1 h, the solvent was removed in vacuo providing a black solid. The solid was transferred to a frit and washed thoroughly with pentane then the solid was dried in vacuo affording 1.46 g of a dark brown solid (with 2 THF molecules by $^1$H NMR. $^1$H NMR (400 MHz, $C_6D_6$): δ12.70 (s, 1H), 11.29 (s, 1H), 8.57 (d, 2H), 6.92 (d, 2H), 6.70 (br. s, 12H), 6.63 9s, 3H), 6.61 (s, 3H), 4.80–4.68 (m, 6H), 3.36 (s, 3H), 2.30–2.20 (m, 36H), 1.00–0.85 (m, 36H).

Example 16
Synthesis of 2-(p-MeOC$_6$H$_4$)-3,4-((3,5-Me$_2$C$_6$H$_4$[i-Pr]N)$_3$MoC)$_2$-2,5-dihydrofuran

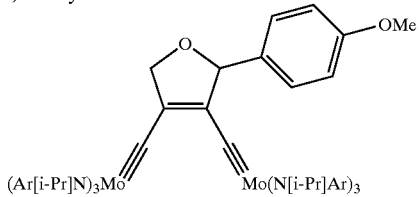

588 mg (0.33 mmol) of the diyne complex prepared above, dissolved in 5.0 mL of THF, was added dropwise by pipette to LiHMDS (111 mg, 0.66 mmol) dissolved in 20 mL of THF. After 30 minutes, the dark-green brown solution was concentrated, pentane was added then concentrated again. The mixture was dissolved in pentane and filtered through Celite. The filtrate was then concentrated, redissolved in pentane and transferred to a 20 mL vial. After being concentrated again, $^1$H NMR analysis shows reaction to be reasonably clean. The mixture was dissolved in minimal volume of pentane and stored in freezer over night during which time a solid precipitates. The yellow-green solid was collected on a frit (202 mg, 44%). The isolated solid was of approximately 90% purity as estimated by NMR analysis. $^1$H NMR: (400 MHz, $C_6D_6$): δ 7.47 (br. d, 2H), 6.98 (br. d, 2H), 6.81 (s, 6H), 6.62 (s, 3H), 6.59 (s, 9H, overlapping peaks), 5.18 (br., 1H), 4.84 (br., 3H), 4.72 (br., 3H), 4.35 (br., 1H), 4.10 (br., 1H), 3.36 (s, 3H), 2.14 (s, 18H), 2.08 (s, 18H), 1.54–1.49 (overlapping d's, 18H), 1.45 (d, 9H), 1.32 (d, 9H).

Example 17
Synthesis of 2-(p-MeOC$_6$H$_4$)-3,4-bis(phenylethynyl)$_2$-2,5-dihydrofuran by three-step procedure

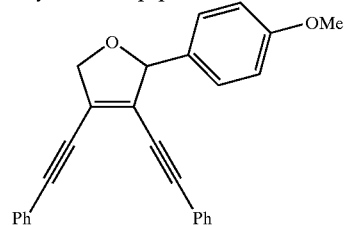

425 mg (0.24 mmol) of the diyne complex prepared above was dissolved in 5 mL of THF and added slowly by pipette to LiHMDS (80 mg, 0.48 mmol) dissolved in 10 mL of THF. After 45 minutes, the mixture was concentrated in vacuo, pentane was added and then the mixture was filtered through Celite. The filtrate was concentrated to a dark green-brown oily solid which was transferred to a 20 mL vial and then concentrated. 246 mg (1.45 mmol) of 2-phenylphenol dissolved in 1 mL of tolune was added leading to a dark red solution. After 1 hour, 258 mg (1.45 mmol) of diphenylacetylene was added and the solution was stirred for 1 hour after which time, 1M HCl was added. The 2-phase mixture was extracted five times with EtOAc then the combined organic layers were dried using $MgSO_4$, concentrated and purified by column chromatography; the enediyne coeluted with 2-phenylphenol. The mixture was dissolved in hexane and extracted 8 times with 1M NaOH to remove the 2-phenylphenol then purified again by column chromatography. 16 mg (18%) of the enediyne was isolated as a pale yellow oil. $^1$H NMR (400 MHz, CDCl$_3$): δ 7.55–7.50 (m, 2H), 7.42–7.35 (m, 7H), 7.33–7.29 (m, 3H), 6.93 (d, J=8.5 Hz, 2H), 5.87 (apparent t, J=4.7 Hz, 1H), 5.04 (dd, J=5.4, 13.1 Hz, 1H), 4.93 (dd, J=3.8 Hz, 13.1 Hz, 1H), 3.83 (s, 3H). $^{13}$C NMR (100 MHz, CDCl$_3$): δ 160.1, 132.7, 132.2, 132.2, 129.6, 129.4, 129.2, 128.9, 128.7, 128.6, 126.1, 123.0, 123.0, 114.3, 99.9, 99.6, 89.9, 82.6, 82.0, 55.7 (one C missing).

Example 18

Synthesis of [((3,5-Me$_2$C$_6$H$_4$[i-Pr]N)$_3$Mo)$_2$(1,6-heptadiyne)]$^{2+}$[I$_2$]$^{2-}$

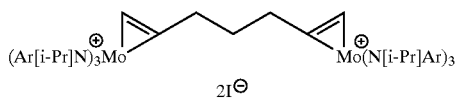

To 2.16 g (3.71 mmol) of the molybdaziridine hydride dissolved in 10 mL of THF was added 470 mg (1.85 mmol) of I$_2$ dissolved in 5 mL of THF. After 30 minutes, 172 mg (1.85 mmol) of 1,6-heptadiyne dissolved in 5 mL of THF was added. After 1 hour, the dark brown solution was concentrated to an oil solid. Pentane was added and then the mixture was concentrated to a yellow-brown solid which was washed thoroughly with pentane on a frit. 2.54 g (91%) of a yellow-brown solid was isolated. $^1$H NMR (300 MHz, C$_6$D$_6$): δ 12.33 (s, 2H), 6.75 (s, 12H), 6.65 (s, 6H), 4.80–4.60 (m, 8H), 2.22 (s, 36H), 1.21 (m, 4H), 0.95 (br. s, 36H).

Example 19

Synthesis of the enediyne, 1,2-bis-phenylethynylcyclopentene (two-step procedure)

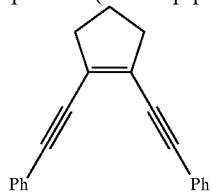

756 mg (0.50 mmol) of the diyne complex prepared above dissolved in 5 mL of THF was added dropwise to LiHMDS dissolved in 10 mL of THF. The reaction mixture was stirred for 30 minutes and then concentrated in vacuo then dissolved in 5 mL of toluene. 456 mg (3.0 mmol) of 1-adamantanol dissolved in 5 mL of toluene was added. After 2 hours, diphenylacetylene (535 mg, 3.0 mmol) was added and the reaction mixture was heated at 115° C. for 24 hours. The reaction mixture was cooled then water was added and the mixture was extracted several times with hexane. The hexane fractions were dried using MgSO$_4$ then concentrated and purified by column chromatography (silica gel, hexanes) affording 134 mg (69%) of the enediyne as a pale yellow solid. $^1$H NMR (300 MHz, CDCl$_3$): δ 7.55–7.50 (m, 4H), 7.38–7.32 (m, 6H), 2.71 (t, J=7.5 Hz, 4H), 2.03 (quint, J=7.6 Hz, 2H).

Example 20

Synthesis of [((3,5-Me$_2$C$_6$H$_4$[i-Pr]N)$_3$Mo)$_2$ (1,7-octadiyne)]$^{2+}$[I$_2$]$^{2-}$

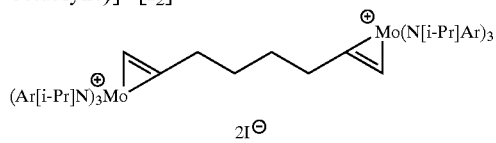

To 2.56 g (4.40 mmol) of the molybdaziridine hydride dissolved in 20 mL of THF was added 558 mg (2.20 mmol) of I$_2$ dissolved in 10 mL of THF. After 1 h, 1,7-octadiyne (223 mg, 2.1 mmol) dissolved in 5 mL of THF was added to the dark green solution. After 2 h, the solution was concentrated in vacuo providing dark brown solid. This solid was washed thoroughly with hexane and then dried in vacuo affording 3.32 g of a golden-brown solid (95% based on 1,7-octadiyne). $^1$H NMR (300 MHz, C$_6$D$_6$): δ 12.42 (s, 2H), 6.71 (s, 12H), 6.63 (s, 6.63), 4.72–4.58 (m, 6H), 4.40–4.20 (br. s, 4H), 2.98–2.80 br. s, 4H), 2.24 (s, 36H), 0.90 (d, 36H).

Example 21

Synthesis of 1,2-((3,5-Me$_2$C$_6$H$_4$[i-Pr]N)$_3$MoC)$_2$-cyclohexene

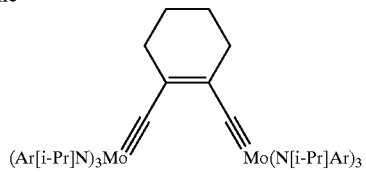

3.05 g (2.0 mmol) of the diyne complex prepared above dissolved in 10 mL of THF was added slowly by pipette to LiHMDS (669 mg, 4.0 mmol) dissolved in 30 mL of THF. After 1 hour, the solution was concentrated to a dark oil. The oil was dissolved in pentane and filtered through Celite on a frit, the Celite was washed thoroughly with pentane. The filtrate was concentrated, redissolved in pentane and stored in the freezer. Over night, 1.2 g (47%) of a brown solid precipitated and was collected. $^1$H NMR (300 MHz, C$_6$D$_6$): 6.82 (s, 12H), 6.61 (s, 6H), 4.94 (m, 6H), 2.14 (s, 36H), 1.76 (m, 4H), 1.49 (d, 36H), 1.18 (m, 4H). $^{13}$C NMR (75 MHz, C$_6$D$_6$): 301.9, 151.5, 139.9, 137.2, 126.4, 125.8, 62.0, 30.2, 25.6, 23.0, 21.6.

Example 22

Synthesis of 1,2-bis-phenylethynylcyclohexene (three step procedure)

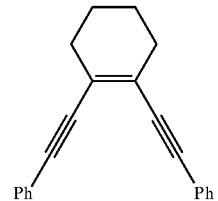

763 mg (0.5 mmol) of the diyne complex prepared above was dissolved in 5 mL of THF and added dropwise by pipette to LiHMDS (167 mg, 1.0 mmol) dissolved in 10 mL of THF. After 30 minutes, 2-phenylphenol (510 mg, 3.0 mmol) was added as a solid, the solution becoming deep red in color. After 2 hours, diphenylacetylene (534 mg, 3.0 mmol) was added as a solid. After 1 hour, H$_2$O was added and the mixture was then extracted several times with EtOAc. Purification of the concentrated mixture by column chromatography provided 40 mg (29%) of a pale yellow solid. $^1$H NMR (400 MHz, CDCl$_3$): δ 7.60 (m, 4H), 7.00–6.89 (m, 6H), 2.26 (m, 4H), 1.28 (m, 4H).

Example 23

Synthesis of the alkyne complex, [(3,5-Me$_2$C$_6$H$_4$[i-Pr]N)$_3$Mo(H—CC-Me)]$^+$[I]$^-$

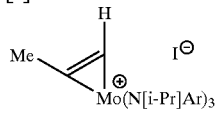

To 2.80 g (4.80 mmol) of molybdaziridine hydride dissolved in 40 mL of hexane was added 609 mg (2.40 mmol) of I$_2$ dissolved in 10 mL of Et$_2$O. After 30 minutes, propyne (175 mL) was transferred through a vacuum line to the reaction mixture. An exothermic reaction ensues and the dark-green reaction mixture becomes orange-brown in color with large amount of precipitate formed. After 30 minutes, the solid was collected on a frit and washed thoroughly with hexane yielding 2.65 g (74%) of a bright yellow solid. $^1$H NMR (300 MHz, C$_6$D$_6$): δ10.90 (s, 1H), 6.78 (s, 6H), 6.67 (s, 3H), 4.90 (m, 3H), 3.00 (s, 3H), 2.25 (s, 18H), 1.03 (d, 18H); $^{13}$C NMR (75 MHz, C$_6$D$_6$): δ 179.3, 172.2 (m), 144.9, 138.8, 130.0, 126.7, 58.3, 25.8, 22.7, 21.7.

Example 24

Synthesis of the enedialkylidyne, (E)-2,3-((3,5-Me$_2$C$_5$H$_4$[i-Pr]N)$_3$MoC)$_2$-but-2-ene

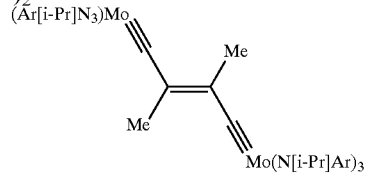

To 2.60 g (3.23 mmol) of the alkyne complex prepared above dissolved in 10 mL of THF was added LiHMDS (541 mg, 3.23 mmol) dissolved in 10 mL THF. The color of the reaction mixture changes from orange-brown to dark brown and was stirred for 1 hour then concentrated in vacuo. The product mixture was then dissolved in hexane and filtered through Celite. Concentration of the filtrate afforded the enedialkylidyne as a green solid (1.61 g). The solid left on the frit was washed again with hexane and after concentration of the filtrate, 330 mg of the enedialkylidyne was isolated (total yield, 97%). $^1$H NMR (300 MHz, C$_6$D$_6$): δ 6.72 (s, 12H), 6.62 (s, 6H), 4.42 (sept., 6H), 2.17 (s, 36H), 1.69 (s, 6H), 1.38 (d, 36H).

Example 25

Synthesis of the enedialkylidyne, (E)-2,3-((1-adamantoxy)$_3$MoC)$_2$-but-2-ene

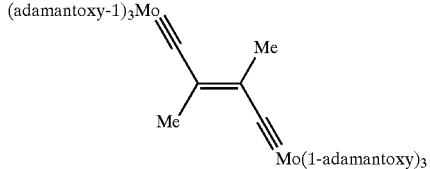

To 1.10 g (0.88 mmol) of the enedialkylidyne prepared above suspended in 15 mL Et$_2$O was added 1-adamantanol (808 mg, 5.31 mmol) as a solid. The yellow-green mixture becomes dark in color. Over 1 h time period, a solid precipitates which was collected by filtration (450 mg). The filtrate was concentrated to a solid and then washed on a frit with hexane affording 320 mg of a solid (total yield is 74%). $^1$H NMR (300 MHz, C$_6$D$_6$): δ2.80 (s, 6H), 2.20–2.05 (br., 54H), 1.58 (q, 18H).

Example 26

Synthesis of (E)-2,3-phenylethynylbut-2-ene (one-step procedure)

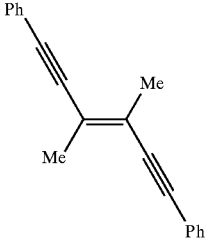

118 mg (0.10 mmol) of enedialkylidyne, (E)-2,3-((1-adamantoxy)$_3$MoC)$_2$-but-2-ene was suspended in 2 mL Et$_2$O and 71 mg (0.40 mmol) of diphenylacetylene dissolved in 1 mL of Et$_2$O was added. The mixture changes from a yellow-green suspension to a red-brown mixture where almost all the solid is dissolved. After 1 hour, the mixture was diluted with H$_2$O and then extracted several times with EtOAc and purified by column chromatography to afford 20 mg (78%) of the enediyne as a white solid. $^1$H NMR (300 MHz, CDCl$_3$): δ 7.48–7.46 (m, 4H), 7.36–7.31 (m, 6H), 2.22 (s, 6H).

Example 27

Alkyne Metathesis Using Enedialkylidynes as Catalyst

Phenylpropyne (465 mg, 4.0 mmol) dissolved in toluene (20 mL) was added to 32 mg (0.04 mmol) of the (2-phenylphenoxy)$_3$MoC-Ph)(THF)$_2$ (see Example 7) dissolved in toluene (20 mL). The reddish-brown mixture was slowly concentrated in vacuo over a period of 60 minutes to remove 2-butyne as it is formed; a room temperature (~24° C.) water bath was used throughout to maintain a constant temperature. The resulting red solid was dissolved in hexanes (~5 mL) and loaded onto a silica column, and eluted with hexanes until the least polar UV active compound was completely eluted from the column. Removal of solvent in vacuo, provided 322 mg (90%) of a white solid. $^1$H NMR spectroscopic analysis and thin layer chromatography established it as diphenylacetylene, the product of metathesis.

Similar procedures were carried out using each of the enedialkylidynes (0.02 mmol) described in Examples 2 and 3 and phenylpropyne (4.0 mmol), leading to 82% and 74% isolated yields of diphenylacetylene, respectively. In the former case, the enedialkylidyne was pretreated with 2-phenylphenol (0.12 mmol, 6 equiv) to generate in situ an active precatalyst.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of preparing an enedialkylidyne complex, comprising:
   (a) combining a terminal alkyne with a first transition metal complex to give a second transition metal complex; and
   (b) treating the second transition metal complex with a base.

2. The method of claim 1, wherein the terminal alkyne is an alpha, omega-dialkyne.

3. The method of claim 1, wherein the first transition metal complex comprises a Group VI transition metal.

4. The method of claim 3, wherein the Group VI transition metal is Mo or W.

5. The method of claim 3, wherein the Group VI transition metal is Mo.

6. The method of claim 1, wherein the first transition metal complex has the formula $X_3MX'$, wherein X is independently for each occurrence a σ-bond ligand;

M is a Group VI transition metal; and

X' is chloride, bromide or iodide.

7. The method of claim 6, wherein X is independently for each occurrence —$N(R)_2$, and R is independently for each occurrence H, alkyl, aryl, aralkyl, cycloalkyl, bicycloalkyl, or tricycloalkyl.

8. The method of claim 7, wherein X is —$N(i\text{-}Pr)(3,5\text{-}Me_2C_6H_3)$.

9. The method of claim 6, wherein X' is I.

10. The method of claim 6, wherein M is Mo or W.

11. The method of claim 6, wherein M is Mo.

12. The method of claim of claim 6, wherein X is —$N(i\text{-}Pr)(3,5\text{-}Me_2C_6H_3)$, M is Mo, and X' is I.

13. A method of preparing an enediyne or an alkyne metathesis catalyst or both, comprising the step of reacting an alkyne with an enedialkylidyne complex, thereby forming an enediyne or an alkyne metathesis catalyst or both.

14. The method of claim 13, wherein the enedialkylidyne complex comprises a Group VI transition metal.

15. The method of claim 14, wherein the Group VI transition metal is Mo or W.

16. The method of claim 14, wherein the Group VI transition metal is Mo.

17. The method of claim 13, wherein the enedialkylidyne complex has formula I or II:

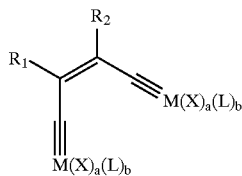

I

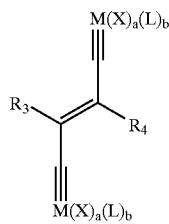

II wherein, independently for each occurrence:

M is a Group V, VI, VII, or VIII transition metal;

X is a σ-bonded ligand:

L is a donor bonded ligand;

$R_1$, $R_2$, $R_3$, and $R_4$ are H, or optionally substituted alkyl, aryl, or aralkyl; or $R_1$ and $R_2$ are covalently bonded to each other to form a 4–20 membered ring;

a is an integer from 1 to 3 inclusive; and b is an integer from 0 to 4 inclusive.

18. The method of claim 17, wherein the enedialkylidyne complex has formula III:

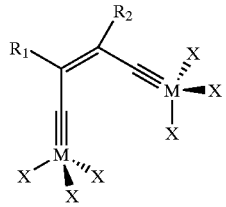

III wherein, independently for each occurrence:

X is a σ-bond ligand;

M is a Group VI transition metal; and $R_1$ and $R_2$ are H, or optionally substituted alkyl, aryl, or aralkyl; or $R_1$ and $R_2$ are covalently bonded to each other to form a 4–20 membered ring.

19. The method of claim 18, wherein X is independently for each occurrence —OR, and R is independently for each occurrence alkyl, aryl, aralkyl, cycloalkyl, bicycloalkyl, or tricycloalkyl.

20. The method of claim 19, wherein R is independently for each occurrence selected from the group consisting of 2-methylphenyl, 2-phenylphenyl, 2,6-diphenylphenyl, 1-adamantanyl, 2-trifluoromethyl-2-propyl, and t-butyl.

21. The method of claim 18, wherein M is independently for each occurrence Mo or W.

22. The method of claim 18, wherein M is Mo.

23. The method of claim 18, wherein $R_1$ and $R_2$ form a six-membered ring.

24. The method of claim 18, wherein X is —O-adamantantyl, M is Mo, and $R_1$ and $R_2$ form a six-membered ring.

25. The method of claim 18, wherein the alkyne metathesis catalyst has formula IV:

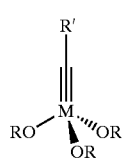

IV wherein

M is a Group VI transition metal;

R is independently for each occurrence H, alkyl, aryl, aralkyl, cycloalkyl, bicycloalkyl, or tricycloalkyl; and R' is optionally substituted alkyl or optionally substituted aryl.

26. The method of claim 25, wherein M is Mo or W.

27. The method of claim 25, wherein M is Mo.

28. The method of claim 25, wherein R is independently for each occurrence selected from the group consisting of 2-methylphenyl, 2-phenylphenyl, 2,6-diphenylphenyl, 1-adamantanyl, 2-trifluoromethyl-2-propyl, and t-butyl.

29. The method of claim 25, wherein M is Mo, and R is independently for each occurrence selected from the group consisting of 2-methylphenyl, 2-phenylphenyl, 2,6-diphenylphenyl, 1-adamantanyl, 2-trifluoromethyl-2-propyl, and t-butyl.

30. A method of catalyzing an alkyne metathesis reaction, comprising combining an alkyne with an enedialkylidyne represented by formula V or VI:

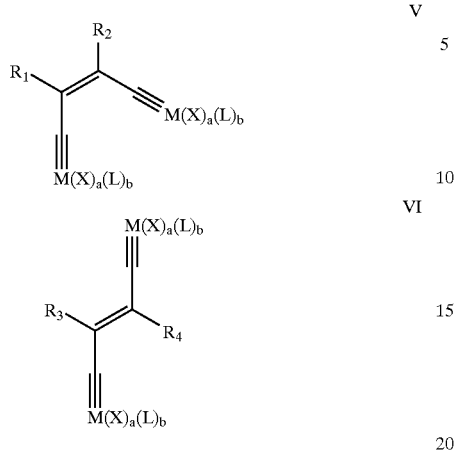

wherein, independently for each occurrence:
  M is a Group V, VI, VII, or VIII transition metal;
  X is a σ-bonded ligand:
  L is a donor bonded ligand;
  $R_1$, $R_2$, $R_3$, and $R_4$ are H, or optionally substituted alkyl, aryl, or aralkyl; or $R_1$ and $R_2$ are covalently bonded to each other to form a 4–20 membered ring;
  a is an integer from 1 to 3 inclusive; and
  b is an integer from 0 to 4 inclusive.

31. The method of claim 30, wherein the enedialkylidyne complex has formula VII:

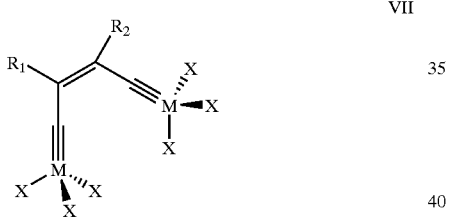

wherein, independently for each occurrence:
  X is —OR;
  R is alkyl, aryl, aralkyl, cycloalkyl, bicycloalkyl, or tricycloalkyl;
  M is a Group VI transition metal; and
  $R_1$ and $R_2$ are H, or optionally substituted alkyl, aryl, or aralkyl; or $R_1$ and $R_2$ are covalently bonded to each other to form a 4–20 membered ring.

32. The method of claim 31, wherein R is independently for each occurrence selected from the group consisting of 2-methylphenyl, 2-phenylphenyl, 2,6-diphenylphenyl, 1-adamantanyl, 2-trifluoromethyl-2-propyl, and t-butyl.

33. The method of claim 31, wherein M is independently for each occurrence Mo or W.

34. The method of claim 31, wherein M is Mo.

35. The method of claim 31, wherein R is independently for each occurrence selected from the group consisting of 2-methylphenyl, 2-phenylphenyl, 2,6-diphenylphenyl, 1-adamantanyl, 2-trifluoromethyl-2-propyl, and t-butyl; and M is Mo.

36. A method of activating an enedialkylidyne complex for metathesis, wherein the endedialkylidyne complex comprises at least one σ-bonded amine ligand, comprising reacting the enedialkylidine complex with an alcohol to form at least one σ-bonded alkoxy ligand.

37. An enedialkylidyne complex having formula VIII, IX, or X:

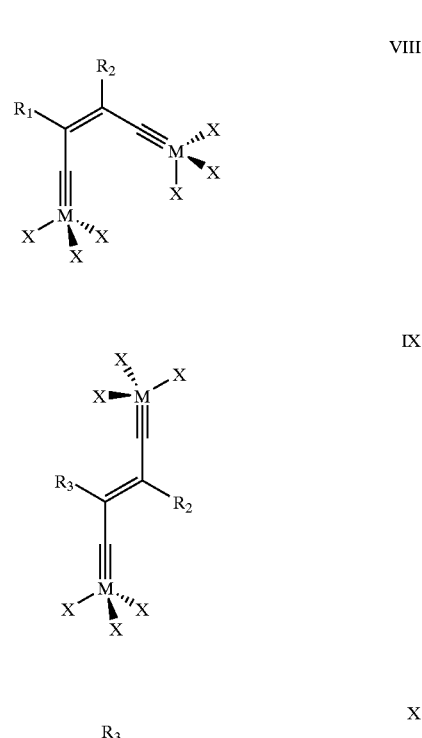

wherein, independently for each occurrence:

M is a Group VI transition metal;

X is a σ-bonded ligand;

$R_1$ and $R_2$ are an optionally substituted alkyl, aryl, or aralkyl; or $R_1$ and $R_2$ are covalently bonded to each other to form a 4–20 membered ring; and $R_3$ is H, or optionally substituted alkyl, aryl, or aralkyl.

38. The compound of claim 37, wherein M is a Mo or W.

39. The compound of claim 37, wherein M is Mo.

40. The compound of claim 37, wherein X is —OR, wherein R is independently for each occurrence alkyl, aryl, cycloalkyl, bicycloalkyl, or tricycloalkyl.

41. The compound of claim 37, wherein X is —N(R)$_2$, wherein R is independently for each occurrence H, alkyl, aryl, cycloalkyl, bicycloalkyl, or tricycloalkyl.

42. The compound of claim 37, wherein X is —N(i-Pr) (3,5-Me$_2$C$_6$H$_3$).

43. The compound of claim 37, wherein $R_1$ and $R_2$ are covalently bonded to each other to form a 4–20 membered ring.

44. The compound of claim 37, wherein the compound is

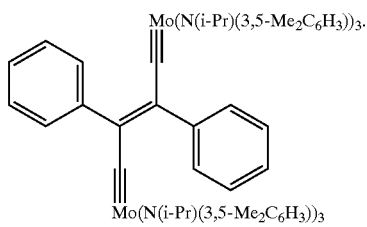

45. The compound of claim 37, wherein the compound is

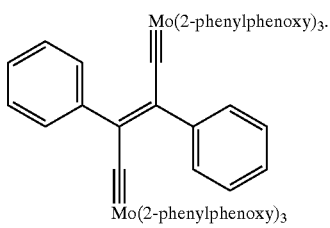

46. The compound of claim 37, wherein the compound is

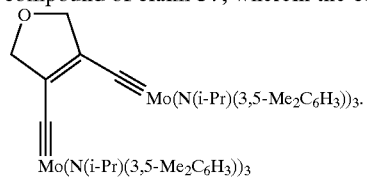

47. The compound of claim 37, wherein the compound is

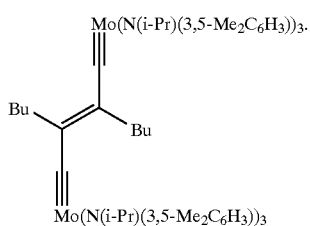

48. The compound of claim 37, wherein the compound is

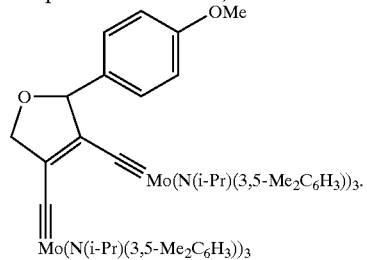

49. The compound of claim 37, wherein the compound is

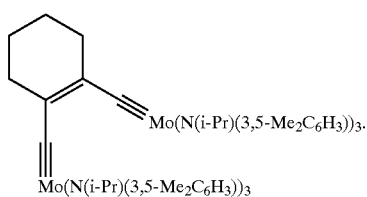

50. The compound of claim 37, wherein the compound is

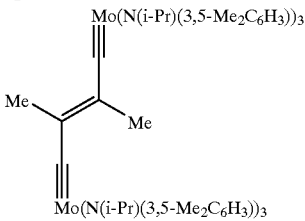

51. The compound of claim 37, wherein the compound is

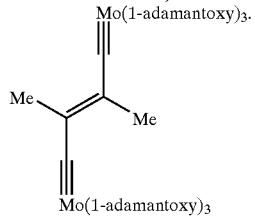

52. The compound of claim 37, wherein the compound is

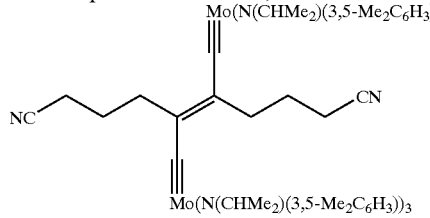

53. The compound of claim 37, wherein the compound is

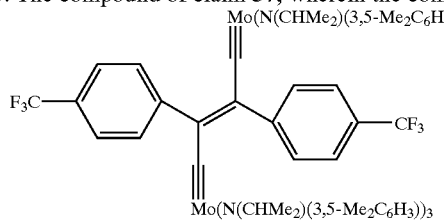

54. The compound of claim 37, wherein the compound is

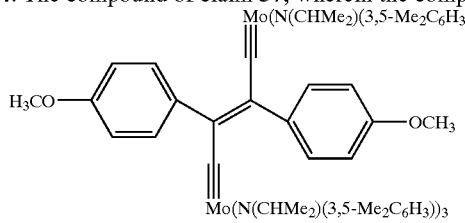

55. The compound of claim 37, wherein the compound is

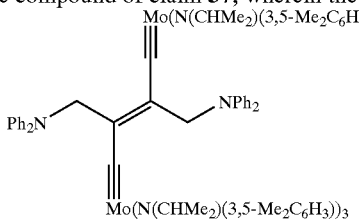

* * * * *